(12) United States Patent
Nankervis

(10) Patent No.: US 11,008,547 B2
(45) Date of Patent: May 18, 2021

(54) PASSIVE REPLACEMENT OF MEDIA

(71) Applicant: Terumo BCT, Inc., Lakewood, CO (US)

(72) Inventor: Brian J. Nankervis, Thornton, CO (US)

(73) Assignee: Terumo BCT, Inc., Lakewood, CO (US)

( * ) Notice: Subject to any disclaimer, the term of this patent is extended or adjusted under 35 U.S.C. 154(b) by 151 days.

(21) Appl. No.: 14/668,659

(22) Filed: Mar. 25, 2015

(65) Prior Publication Data

US 2015/0275170 A1   Oct. 1, 2015

Related U.S. Application Data

(60) Provisional application No. 61/970,274, filed on Mar. 25, 2014.

(51) Int. Cl.
| | |
|---|---|
| *C12N 5/071* | (2010.01) |
| *C12M 1/34* | (2006.01) |
| *C12M 1/12* | (2006.01) |
| *C12M 1/00* | (2006.01) |
| *C12M 1/36* | (2006.01) |
| *C12M 1/42* | (2006.01) |

(52) U.S. Cl.
CPC .......... *C12N 5/0602* (2013.01); *C12M 25/10* (2013.01); *C12M 29/00* (2013.01); *C12M 29/16* (2013.01); *C12M 29/26* (2013.01); *C12M 35/08* (2013.01); *C12M 41/00* (2013.01); *C12M 41/48* (2013.01)

(58) Field of Classification Search
CPC ............. C12M 1/00; C12M 1/12; C12M 1/36
See application file for complete search history.

(56) References Cited

U.S. PATENT DOCUMENTS

| | | |
|---|---|---|
| 3,821,087 A | 6/1974 | Knazek et al. |
| 3,896,061 A | 7/1975 | Tanzawa et al. |
| 4,391,912 A | 7/1983 | Yoshida et al. |
| 4,439,322 A | 3/1984 | Sonoda et al. |
| 4,618,586 A | 10/1986 | Walker et al. |
| 4,629,686 A | 12/1986 | Gruenberg |
| 4,647,539 A | 3/1987 | Bach |
| 4,650,766 A | 3/1987 | Harm et al. |
| 4,722,902 A | 2/1988 | Harm et al. |
| 4,804,628 A | 2/1989 | Cracauer et al. |
| 4,885,087 A | 12/1989 | Kopf |
| 4,889,812 A | 12/1989 | Guinn et al. |
| 4,894,342 A | 1/1990 | Guinn et al. |
| 4,918,019 A | 4/1990 | Guinn |
| 4,973,558 A | 11/1990 | Wilson et al. |
| 5,079,168 A | 1/1992 | Amiot |
| 5,126,238 A | 6/1992 | Gebhard et al. |
| 5,162,225 A | 11/1992 | Sager et al. |
| 5,202,254 A | 4/1993 | Amiot |
| 5,330,915 A | 7/1994 | Wilson et al. |
| 5,399,493 A | 3/1995 | Emerson et al. |
| 5,416,022 A | 5/1995 | Amiot |
| 5,437,994 A | 8/1995 | Emerson et al. |
| 5,459,069 A | 10/1995 | Palsson et al. |
| 5,510,257 A | 4/1996 | Sirkar et al. |
| 5,541,105 A | 7/1996 | Melink et al. |
| 5,605,822 A | 2/1997 | Emerson et al. |
| 5,622,857 A | 4/1997 | Goffe |
| 5,631,006 A | 5/1997 | Melink et al. |
| 5,635,386 A | 6/1997 | Palsson et al. |
| 5,635,387 A | 6/1997 | Fei et al. |
| 5,646,043 A | 7/1997 | Emerson et al. |
| 5,656,421 A | 8/1997 | Gebhard et al. |
| 5,670,147 A | 9/1997 | Emerson et al. |
| 5,670,351 A | 9/1997 | Emerson et al. |
| 5,688,687 A | 11/1997 | Palsson et al. |
| 5,763,194 A | 6/1998 | Slowiaczek et al. |
| 5,763,261 A | 6/1998 | Gruenberg |

(Continued)

FOREIGN PATENT DOCUMENTS

| | | |
|---|---|---|
| CN | 102406926 A | 4/2012 |
| DE | 3833925 A1 | 9/1989 |

(Continued)

OTHER PUBLICATIONS

Communication pursuant to Article 94(3) EPC, European Patent Application No. 15718657.8, dated Jul. 21, 2017.
Communication pursuant to Article 94(3) EPC, European Patent Application No. 15718657.8, dated Mar. 22, 2018.
First Office Action, Chinese Patent Application No. 201580020869.5, dated Apr. 27, 2018 (English language translation included).
International Search Report and Written Opinion, PCT/US2015/022541, dated Jul. 17, 2015.
Rejection of the Application, Japanese Patent Application No. 2016-558755, dated Feb. 5, 2019 (English language translation included).

(Continued)

*Primary Examiner* — Teresa E Knight
(74) *Attorney, Agent, or Firm* — Terumo BCT, Inc. IP Law Department

(57) ABSTRACT

Embodiments described herein generally relate to passively replacing media in a closed cell expansion system to reduce or prevent the dilution of chemical signaling used to inhibit signaling pathways that keep a cell population in the lag phase of cell growth. To prevent such dilution, active inlet fluid flow to the system may be halted. To replace fluid lost by the system, a bag containing media may be attached to the waste line in replacement of the waste or outlet bag connected thereto. By turning off one or more pumps, media from the replacement bag is added to the system at the rate of evaporation. Chemical signaling dilution may be prevented while conserving system resources. Enhancement of chemical signaling to reduce the lag phase of cell growth may further be accomplished by adding molecules, such as chemical-signaling proteins, from a direct source to the system.

20 Claims, 13 Drawing Sheets

(56) References Cited

U.S. PATENT DOCUMENTS

| | | |
|---|---|---|
| 5,763,266 A | 6/1998 | Palsson et al. |
| 5,882,918 A | 3/1999 | Goffe |
| 5,888,807 A | 3/1999 | Palsson et al. |
| 5,958,763 A | 9/1999 | Goffe |
| 5,981,211 A | 11/1999 | Hu et al. |
| 5,985,653 A | 11/1999 | Armstrong et al. |
| 5,994,129 A | 11/1999 | Armstrong et al. |
| 5,998,184 A | 12/1999 | Shi |
| 6,001,585 A | 12/1999 | Gramer |
| 6,048,721 A | 4/2000 | Armstrong et al. |
| 6,096,532 A | 8/2000 | Armstrong et al. |
| 6,228,635 B1 | 5/2001 | Armstrong et al. |
| 6,238,908 B1 | 5/2001 | Armstrong et al. |
| 6,326,198 B1 | 12/2001 | Emerson et al. |
| 6,566,126 B2 | 5/2003 | Cadwell |
| 6,582,955 B2 | 6/2003 | Martinez et al. |
| 6,616,912 B2 | 9/2003 | Eddleman et al. |
| 6,642,019 B1 | 11/2003 | Anderson et al. |
| 6,667,034 B2 | 12/2003 | Palsson et al. |
| 6,835,566 B2 | 12/2004 | Smith et al. |
| 6,844,187 B1 | 1/2005 | Wechsler et al. |
| 6,943,008 B1 | 9/2005 | Ma |
| 6,969,308 B2 | 11/2005 | Doi et al. |
| 6,979,308 B1 | 12/2005 | McDonald et al. |
| 7,033,823 B2 | 4/2006 | Chang |
| 7,041,493 B2 | 5/2006 | Rao |
| 7,112,441 B2 | 9/2006 | Uemura et al. |
| 7,172,696 B1 | 2/2007 | Martinez et al. |
| 7,270,996 B2 | 9/2007 | Cannon et al. |
| 7,531,351 B2 | 5/2009 | Marx et al. |
| 7,534,601 B2 | 5/2009 | Wikswo et al. |
| 7,682,822 B2 | 3/2010 | Noll et al. |
| 7,718,430 B2 | 5/2010 | Antwiler |
| 8,288,159 B2 | 10/2012 | Warren et al. |
| 8,298,823 B2 | 10/2012 | Warren et al. |
| 8,309,347 B2 | 11/2012 | Antwiler |
| 8,383,397 B2 | 2/2013 | Wojciechowski et al. |
| 8,399,245 B2 | 3/2013 | Leuthaeuser et al. |
| 8,540,499 B2 | 9/2013 | Page et al. |
| 8,785,181 B2 | 7/2014 | Antwiler |
| 8,895,291 B2 | 11/2014 | DiLorenzo et al. |
| 9,057,045 B2 | 6/2015 | Gibbons et al. |
| 9,109,193 B2 | 8/2015 | Galliher et al. |
| 9,175,259 B2 | 11/2015 | Nankervis |
| 9,441,195 B2 | 9/2016 | Wojciechowski et al. |
| 9,534,198 B2 | 1/2017 | Page et al. |
| 9,732,313 B2 | 8/2017 | Hirschel et al. |
| 10,093,956 B2 | 10/2018 | Hirschel et al. |
| 10,494,421 B2 | 12/2019 | Castillo |
| 2004/0027914 A1 | 2/2004 | Vrane |
| 2006/0019388 A1 | 1/2006 | Hutmacher et al. |
| 2006/0166364 A1 | 7/2006 | Senesac |
| 2006/0233834 A1 | 10/2006 | Guehenneux et al. |
| 2007/0122904 A1 | 5/2007 | Nordon |
| 2007/0160583 A1 | 7/2007 | Lange et al. |
| 2007/0231305 A1 | 10/2007 | Noll et al. |
| 2007/0298497 A1 | 12/2007 | Antwiler |
| 2008/0050770 A1 | 2/2008 | Zhang et al. |
| 2008/0220522 A1 | 9/2008 | Antwiler |
| 2008/0220523 A1* | 9/2008 | Antwiler ................ C12M 25/10 435/394 |
| 2008/0227190 A1 | 9/2008 | Antwiler |
| 2008/0248572 A1 | 10/2008 | Antwiler |
| 2008/0254533 A1 | 10/2008 | Antwiler |
| 2009/0215022 A1 | 8/2009 | Page et al. |
| 2009/0269841 A1 | 10/2009 | Wojciechowski et al. |
| 2010/0042260 A1 | 2/2010 | Antwiler |
| 2010/0105138 A1 | 4/2010 | Dodd et al. |
| 2010/0144037 A1 | 6/2010 | Antwiler |
| 2011/0159584 A1* | 6/2011 | Gibbons ................ C12M 23/42 435/325 |
| 2011/0212493 A1 | 9/2011 | Hirschel et al. |
| 2012/0086657 A1* | 4/2012 | Stanton, IV ........... C12M 23/42 345/173 |
| 2012/0315696 A1 | 12/2012 | Luitjens et al. |
| 2013/0058907 A1 | 3/2013 | Wojciechowski et al. |
| 2013/0143313 A1 | 6/2013 | Niazi |
| 2015/0111252 A1 | 4/2015 | Hirschel et al. |
| 2015/0175950 A1 | 6/2015 | Hirschel et al. |
| 2015/0225685 A1 | 8/2015 | Hirschel et al. |
| 2015/0259749 A1 | 9/2015 | Santos et al. |
| 2016/0362650 A1 | 12/2016 | Wojciechowski et al. |
| 2016/0362652 A1 | 12/2016 | Page et al. |
| 2018/0010082 A1 | 1/2018 | Jaques et al. |
| 2018/0030398 A1 | 2/2018 | Castillo |
| 2018/0155668 A1 | 6/2018 | Hirschel et al. |
| 2019/0194628 A1 | 6/2019 | Rao et al. |

FOREIGN PATENT DOCUMENTS

| | | |
|---|---|---|
| EP | 0220650 A2 | 5/1987 |
| EP | 2027247 B1 | 1/2011 |
| EP | 2481819 A1 | 8/2012 |
| JP | H02245177 A | 9/1990 |
| JP | 2003510068 A | 3/2003 |
| JP | 2005278564 A | 10/2005 |
| JP | 2007000038 A | 1/2007 |
| JP | 2012506257 A | 3/2012 |
| JP | 5548207 B2 | 7/2014 |
| JP | 2019516029 A | 6/2019 |
| JP | 2019525765 A | 9/2019 |
| KR | 101228026 B1 | 1/2013 |
| KR | 20150002762 A | 1/2015 |
| KR | 101504392 B1 | 3/2015 |
| KR | 101548790 B1 | 8/2015 |
| KR | 101553040 B1 | 9/2015 |
| KR | 20170076679 A | 7/2017 |
| KR | 20180027501 A | 3/2018 |
| KR | 102027596 B1 | 10/2019 |
| KR | 20200034790 A | 3/2020 |
| KR | 20200058433 A | 5/2020 |
| WO | 86/02379 A1 | 4/1986 |
| WO | 88/01643 A1 | 3/1988 |
| WO | 89/12676 A1 | 12/1989 |
| WO | 90/02171 A1 | 3/1990 |
| WO | 91/07485 A1 | 5/1991 |
| WO | 92/10564 A1 | 6/1992 |
| WO | 95/04813 A1 | 2/1995 |
| WO | 95/21911 A1 | 8/1995 |
| WO | 95/24468 A1 | 9/1995 |
| WO | 97/16527 A1 | 5/1997 |
| WO | 98/22588 A2 | 5/1998 |
| WO | 98/53046 A1 | 11/1998 |
| WO | 00/46354 A1 | 8/2000 |
| WO | 00/75275 A2 | 12/2000 |
| WO | 01/23520 A1 | 4/2001 |
| WO | 02/28996 A1 | 4/2002 |
| WO | 03/039459 A2 | 5/2003 |
| WO | 03/105663 A2 | 12/2003 |
| WO | 2004/090112 A2 | 10/2004 |
| WO | 2005087915 A2 | 9/2005 |
| WO | 2005/104755 A2 | 11/2005 |
| WO | 2006/037022 A2 | 4/2006 |
| WO | 2007/038572 A2 | 4/2007 |
| WO | 2007/059473 A2 | 5/2007 |
| WO | 2007/117765 A2 | 10/2007 |
| WO | 2007/136821 A1 | 11/2007 |
| WO | 2007/139742 A1 | 12/2007 |
| WO | 2007/139746 A1 | 12/2007 |
| WO | 2007/139747 A1 | 12/2007 |
| WO | 2007/139748 A2 | 12/2007 |
| WO | 2008/073635 A2 | 6/2008 |
| WO | 2008/109674 A2 | 9/2008 |
| WO | 2009/034186 A2 | 3/2009 |
| WO | 2010/036760 A1 | 4/2010 |
| WO | 2011/098592 A1 | 8/2011 |
| WO | 2011/130617 A2 | 10/2011 |
| WO | 2012/171026 A2 | 12/2012 |
| WO | 2012/171030 A2 | 12/2012 |
| WO | 2013/085682 A1 | 6/2013 |
| WO | 2015/059714 A1 | 4/2015 |
| WO | 2015/069943 A1 | 5/2015 |
| WO | 2015/073913 A1 | 5/2015 |
| WO | 2015/118148 A1 | 8/2015 |

(56) References Cited

FOREIGN PATENT DOCUMENTS

| WO | 2015/118149 A1 | 8/2015 |
| WO | 2016/130940 A1 | 8/2016 |
| WO | 2017/072201 A2 | 5/2017 |
| WO | 2017/158611 A1 | 9/2017 |
| WO | 2017/207822 A1 | 12/2017 |
| WO | 2018/183426 A1 | 10/2018 |
| WO | 2019/155032 A1 | 8/2019 |
| WO | 2019/238919 A1 | 12/2019 |
| WO | 2020/020569 A1 | 1/2020 |
| WO | 2020/079274 A1 | 4/2020 |

OTHER PUBLICATIONS

Rejection of the Application, Japanese Patent Application No. 2016-558755, dated Jan. 28, 2020 (English language translation included).

Second Office Action, Chinese Patent Application No. 201580020869.5, dated May 21, 2019 (English language translation included).

Third Office Action, Chinese Patent Application No. 201580020869.5, dated Nov. 6, 2019 (English language translation included).

Garlie et al., "T Cells Coactivated with Immobilized Anti-CD3 and Anti-CD28 as Potential Immunotherapy for Cancer," Journal of Immunotherapy, vol. 22, No. 4, pp. 336-345, 1999.

GE Healthcare UK Limited, "The Effect of Rocking Rate and Angle on T Cell Cultures Grown in Xuri(TM) Cell Expansion Systems," Cell therapy bioreactor systems, Application note 29-1166-55 AA, pp. 1-4, www.gelifesciences.com/xuri, Aug. 2014.

Ueda et al., "Interaction of Natural Killer Cells with Neutrophils Exerts a Significant Antitumor Immunity in Hematopoietic Stem Cell Transplantation Recipients," Cancer Medicine, vol. 5, No. 1, pp. 49-60, 2016.

Urbich et al., "Fluid Shear Stress-induced Transcriptional Activation of the Vascular Endothelial Growth Factor Receptor-2 Gene Requires Sp1-Dependent DNA Binding," FEBS Letters, 535, pp. 87-93, 2003.

Von Laer, D., "Loss of CD38 Antigen on CD34 CD38 Cells during Short-term Culture," Leukemia, Correspondence, pp. 947-948, 1999.

Wagner et al., "Phase I/II Trial of StemRegenin-1 Expanded Umbilical Cord Blood Hematopoietic Stem Cells Supports Testing as a Stand-alone Graft," Cell Stem Cell, vol. 18, pp. 144-155, Jan. 7, 2016.

Weaver et al., "An Analysis of Engraftment Kinetics as a Function of the CD34 Content of Peripheral Blood Progenitor Cell Collections in 692 Patients after the Administration of Myeloablative Chemotherapy," Blood, vol. 86, No. 10, pp. 3961-3969, Nov. 15, 1995.

Yang et al., "Suspension Culture of Mammalian Cells Using Thermosensitive Microcarrier that Allows Cell Detachment without Proteolytic Enzyme Treatment," Cell Transplantation, vol. 19, pp. 1123-1132, Aug. 18, 2010.

Yi et al., "A Readily Modified Polyethersulfone with Amino-Substituted Groups: Its Amphiphilic Copolymer Synthesis and Membrane Application," Polymer, vol. 53, pp. 350-358, Dec. 2, 2011.

Zheng et al., "Differential Effects of Cyclic and Static Stretch on Coronary Microvascular Endothelial Cell Receptors and Vasculogenic/Angiogenic Responses," American Journal of Physiology—Heart and Circulatory Physiology, vol. 295, H794-H800, Aug. 2008.

Gloeckner, H., et al., "New Miniaturized Hollow-Fiber Bioreactor for in Vivo Like Cell Culture, Cell Expansion, and Production of Cell-Derived Products," Biotechnol. Prog., vol. 17, No. 5, pp. 828-831, Aug. 21, 2001.

Chang et al., "Membrane Bioreactors: Present and Prospects", Advances in Biochemical Engineering, 1991, pp. 27-64, vol. 44.

Chang, Ho Nam, "Membrane Bioreactors: Engineering Aspects", Biotech. Adv., 1987, pp. 129-145, vol. 5.

Edgington, Stephen M., "New Horizons for Stem-Cell Bioreactors", Biotechnology, Oct. 1992, pp. 1099-1106, vol. 10.

Gastens et al., "Good Manufacturing Practice-Compliant Expansion of Marrow-Derived Stem and Progenitor Cells for Cell Therapy", Cell Transplantation, 2007, pp. 685-696, vol. 16.

Gramer et al., "Screening Tool for Hollow-Fiber Bioreactor Process Development", Biotechnol. Prog., 1998, pp. 203-209, vol. 14.

Hirschel et al., "An Automated Hollow Fiber System for the Large Scale Manufacture of Mammalian Cell Secreted Product", Large Scale Cell Culture Technology, ed. Bjorn K. Lydersen, 1987, pp. 113-144, Hanser Publishers.

Infanger et al., "Simulated weightlessness changes the cytoskeleton and extracellular matrix proteins in papillary thyroid carcinoma cells", Cell and Tissue Research, 2006, 324(2): 267-277.

Jones et al., "Genetic stability of bone marrow-derived human mesenchymal stromal cells in the Quantum System", Cytotherapy, 2013; 15: 1323-1339.

Liu et al., "Ex vivo Expansion of Hematopoietic Stem Cells Derived from Umbilical Cord Blood in Rotating Wall Vessel", Journal of Biotechnology, 2006, 124:592-601.

Nankervis et al., "Shear Stress Conditions in the Quantum Cell Expansion System", Poster Session—TERMIS AM Annual Conference 2013, Nov. 12, 2013.

Nguyen et al., "Quantum® Cell Expansion System: Automated Expansion of Human Mesenchymal Stem Cells from Precultured Cells Using the Quantum Cell Expansion System", Terumo BCT, Inc., 2012.

Nielsen, Lars Keld, "Bioreactors for Hematopoietic Cell Culture", Annu. Rev. Biomed. Eng., 1999, vol. 1, pp. 129-152.

Office Action, Chinese Patent Application No. 201580020869.5, dated Apr. 27, 2018. (English language translation included).

Office Action, Chinese Patent Application No. 201580020869.5, dated May 21, 2019. (English language translation included).

Official Communication, European Patent Application No. 15718657.8, dated Jul. 21, 2017.

Official Communication, European Patent Application No. 15718657.8, dated Mar. 22, 2018.

Pörtner et al., "An Overview on Bioreactor Design, Prototyping and Process Control for Reproducible Three-Dimensional Tissue Culture", Drug Testing in Vitro: Breakthroughs and Trends in Cell Culture Technology, ed. Uwe Marx and Volker Sandig, 2007, Wiley-VCH, pp. 53-78.

The Extended European Search Report, European Patent Application No. 19202519.5, dated Nov. 15, 2019.

Zhao et al., "Perfusion Bioreactor System for Human Mesenchymal Stem Cell Tissue Engineering: Dynamic Cell Seeding and Construct Development", Biotechnology and Bioengineering, Aug. 20, 2005, vol. 91, No. 4, pp. 482-493.

Abumiya et al., "Shear Stress Induces Expression of Vascular Endothelial Growth Factor Receptor Flk-1/KDR Through the CT-Rich Sp1 Binding Site," Ateriosclerosis, Thrombosis, and Vascular Biology, vol. 22, pp. 907-913, Jun. 2002.

Akiyama et al., "Ultrathin Poly(N-isopropylacrylamide) Grafted Layer on Polystyrene Surfaces for Cell Adhesion/ Detachment Control," Langmuir, vol. 20, No. 13, pp. 5506-5511, May 26, 2004.

Akram et al., "Mesenchymal Stem Cells Promote Alveolar Epithelial Cell Wound Repair in vitro through Distinct Migratory and Paracrine Mechanisms," Respiratory Research, vol. 14, No. 9, pp. 1-16, 2013.

Alenazi et al., "Modified Polyether-sulfone Membrane: a Mini Review," Designed Monomers and Polymers, vol. 20, No. 1, pp. 532-546, 2017.

Anamelechi et al., "Streptavidin Binding and Endothelial Cell Adhesion to Biotinylated Fibronectin," Langmuir, vol. 23, No. 25, pp. 12583-12588, Dec. 4, 2007.

Azar et al., "Heart Rates of Male and Female Sprague-Dawley and Spontaneously Hypertensive Rats Housed Singly or in Groups," Journal of the American Association for Laboratory Animal Science, vol. 50, No. 2, pp. 175-184, Mar. 2011.

Bai et al., "Expansion of Primitive Human Hematopoietic Stem Cells by Culture in a Zwitterionic Hydrogel," Nature Medicine, vol. 25, pp. 1566-1575, Oct. 2019.

Barker et al., "CD34+ Cell Content of 126 341 Cord Blood Units in the US Inventory: Implications for Transplantation and Banking," Blood Advances, vol. 3, No. 8, pp. 1267-1271, Apr. 23, 2019.

(56) References Cited

OTHER PUBLICATIONS

Beacher-Allan et al., "CD4+CD25high Regulatory Cells in Human Peripheral Blood," The Journal of Immunology, vol. 167, pp. 1245-1253, 2001.
Boitano et al., "Aryl Hydrocarbon Receptor Antagonists Promote the Expansion of Human Hematopoietic Stem Cells," Science, vol. 329, No. 5997, pp. 1345-1348, Sep. 10, 2010. Corrected May 6, 2011.
Brunstein et al., "Infusion of ex vivo Expanded T Regulatory Cells in Adults Transplanted with Umbilical Cord Blood: Safety Profile and Detection Kinetics," Blood, vol. 117, No. 3, pp. 1061-1070, Jan. 20, 2011.
Bryce et al., "In vitro Micronucleus Assay Scored by Flow Cytometry Provides a Comprehensive Evaluation of Cytogenetic Damage and Cytotoxicity," Mutation Research, vol. 630, pp. 78-91, Mar. 19, 2007.
Bryce et al., "Interlaboratory Evaluation of a Flow Cytometric, High Content in vitro Micronucleus Assay," Mutation Research, vol. 650, pp. 181-195, Jan. 7, 2008.
Camacho Villa et al., "CD133+CD34+ and CD133+CD38+ Blood Progenitor Cells as Predictors of Platelet Engraftment in Patients Undergoing Autologous Peripheral Blood Stem Cell Transplantation," Transfusion and 4pheresis Science, vol. 46, pp. 239-244, 2012.
Cano et al., "Immobilization of endo-1,4-β-xylanase on Polysulfone Acrylate Membranes: Synthesis and Characterization," Journal of Membrane Science, vol. 280, pp. 383-388, Feb. 28, 2006.
Carvell and Dowd, "On-line Measurements and Control of Viable Cell Density in Cell Culture Manufacturing Processes Using Radio Frequency Impedance," Cytotechnology, vol. 50, pp. 35-48, 2006.
Carvell et al., "Monitoring Live Biomass in Disposable Bioreactors," BioProcess International, vol. 14, No. 3, pp. 10-48, Mar. 2016.
Cuchiara et al., "Covalent Immobilization of SCF and SDF1α for in vitro Culture of Hematopoietic Progenitor Cells," Acta Biomaterials, vol. 9, No. 12, pp. 9258-9269, Dec. 2013.
Da Silva et al., "Smart Thermoresponsive Coatings and Surfaces for Tissue Engineering: Switching Cell-Material Boundaries," Trends in Biotechnology, vol. 15, No. 12, pp. 577-583, 2007.
Hao et al., "A Functional Comparison of CD34+ CD38—Cells in Cord Blood and Bone Marrow," Blood, vol. 86, No. 10, pp. 3745-3753, Nov. 15, 1995.
Harimoto et al., "Novel Approach for Achieving Double-Layered Cell Sheets Co-Culture: Overlaying Endothelial Cell Sheets onto Monolayer Hepatocytes Utilizing Temperature-Responsive Culture Dishes," Journal of Biomedical Material Research, vol. 62, pp. 464-470, 2002.
Högstedt et al., "Frequency and Size Distribution of Micronuclei in Lymphocytes Stimulated with Phytohemagglutinin and Pokeweed Mitogen in Workers Exposed to Piperazine," Hereditas, vol. 109, pp. 139-142, 1988.
Horwitz et al., "Phase I/II Study of Stem-Cell Transplantation Using a Single Cord Blood Unit Expanded Ex Vivo with Nicotinamide," Journal of Clinical Oncology, vol. 37, No. 5, pp. 367-376, Dec. 4, 2018.
Itkin and Lapidot, "SDF-1 Keeps HSC Quiescent at Home," Blood, vol. 117, No. 2, pp. 373-374, Jan. 13, 2011.
Jang et al., "Syndecan-4 Proteoliposomes Enhance Fibroblast Growth Factor-2 (FGF-2)-Induced Proliferation, Migration, and Neovascularization of Ischemic Muscle," PNAS, vol. 109, No. 5, pp. 1679-1684, Jan. 31, 2012.
Johansson et al., "Pancreatic Islet Survival and Engraftment is Promoted by Culture on Functionalized Spider Silk Matrices," PLoS One, pp. 1-21, Jun. 19, 2015.
Klein et al., "Affinity Membranes Prepared from Hydrophilic Coatings on Microporous Polysulf One Hollow Fibers," Journal of Membrane Science, vol. 90, pp. 69-80, 1994.
Koestenbauer et al., "Protocols for Hematopoietic Stem Cell Expansion from Umbilical Cord Blood," Cell Transplantation, vol. 18, pp. 1059-1068, May 6, 2009.
Koller et al., "Clinical-scale Human Umbilical Cord Blood Cell Expansion in a Novel Automated Perfusion Culture System," Bone Marrow Transplantation, vol. 21, pp. 653-663, 1998.
Lang et al., "Generation of Hematopoietic Humanized Mice in the Newborn BALB/C-Rag2null Il2rynull Mouse Model: A Multivariable Optimization Approach," Clinical Immunology, vol. 140, pp. 102-116, Apr. 14, 2011.
Lataillade et al., "Chemokine SDF-1 Enhances Circulating CD341 Cell Proliferation in Synergy with Cytokines: Possible Role in Progenitor Survival," Blood, vol. 95, No. 3, pp. 756-768, Feb. 1, 2000.
Lee et al., "Long-Term Outcomes Following CD19 CART Cell Therapy for B-All Are Superior in Patients Receiving a Fludarabine/Cyclophosphamide Preparative Regimen and Post-CAR Hematopoietic Stem Cell Transplantation," Blood, vol. 128, No. 22, Ab. 218, Dec. 2, 2016.
Li et al., "Heparin-induced Conformation Changes of Fibronectin within the Extracellular Matrix Promote hMSC Osteogenic Differentiation," Biomaterials Science, vol. 3, pp. 73-84, 2015.
Malin et al., "Noninvasive Prediction of Glucose by Near-Infrared Diffuse Reflectance Spectroscopy," Clinical Chemistry, vol. 45, No. 9, 1651-1658, 1999.
Marek-Trzonkowska et al., "Administration of CD4+ CD25high CD127—Regulatory T Cells Preserves β-Cell Function in Type 1 Diabetes in Children," Diabetes Care, vol. 35, No. 9, pp. 1817-1820, Sep. 2012.
Murugappan et al., "Human Hematopoietic Progenitor Cells Grow Faster under Rotational Laminar Flows," Biotechnology Progress—Cell Culture & Tissue Engineering, Online, Apr. 22, 2010.
Nelson et al., "Emergent Patterns of Growth Controlled by Multicellular Form and Mechanics," PNAS, vol. 102, No. 33, pp. 11594-11599, Aug. 16, 2005.
Nicolette et al., "In Vitro Micronucleus Screening of Pharmaceutical Candidates by Flow Cytometry in Chinese Hamster V79 Cells," Environmental and Molecular Mutagenesis, vol. 52, pp. 355-362, Oct. 20, 2010.
Nugent et al., "Adventitial Endothelial Implants Reduce Matrix Metalloproteinase-2 Expression and Increase Luminal Diameter in Porcine Arteriovenous Grafts," Journal of Vascular Surgery, vol. 46, No. 3, pp. 548-556.e2, Sep. 2007.
Okano et al., "Mechanism of Cell Detachment from Temperature-Modulated, Hydrophilic-Hydrophobic Polymer Surfaces," Biomaterials, vol. 16, No. 4, pp. 297-303, 1995.
Putnam et al., "Expansion of Human Regulatory T-Cells from Patients with Type 1 Diabetes," Diabetes, vol. 58, pp. 652-662, Mar. 2009.
Rahmahwati et al., "The Synthesis of Polyethersulfone (PES) Derivatives for the Immobilization of Lipase Enzyme," Key Engineering Materials, vol. 811, pp. 14-21, Jul. 8, 2019.
Rodrigues et al., "Stem Cell Cultivation in Bioreactors," Biotechnology Advances, vol. 29, pp. 815-829, Jun. 25, 2011.
Ronco et al., "Blood and Dialysate Flow Distributions in Hollow-Fiber Hemodialyzers Analyzed by Computerized Helical Scanning Technique," Journal of the American Society of Nephrology, vol. 13, pp. S53-S61, 2002.
Ryu and Gomelsky, "Near-infrared Light Responsive Synthetic c-di-GMP Module for Optogenetic Applications," ACS Synthetic Biology, vol. 3, pp. 802-810, Jan. 28, 2014.
Shimizu et al., "Fabrication of Pulsatile Cardiac Tissue Grafts Using a Novel 3-Dimensional Cell Sheet Manipulation Technique and Temperature-Responsive Cell Culture Surfaces," Circulation Research, vol. 90, e40-e48, pp. 1-9, Feb. 22, 2002.
Smith et al., "Expansion of Neutrophil Precursors and Progenitors in Suspension Cultures of CD34+ Cells Enriched from Human Bone Marrow," Experimental Hematology, vol. 21, pp. 870-877, 1993.
Streltsova et al., "Recurrent Stimulation of Natural Killer Cell Clones with K562 Expressing Membrane-Bound Interleukin-21 Affects Their Phenotype, Interferon-γ Production, and Lifespan," International Journal of Molecular Sciences, vol. 20, No. 443, pp. 1-18, 2019.
Takezawa et al., "Cell Culture on a Thermo-responsive Polymer Surface," Nature, Bio/Technology, vol. 8, pp. 354-856, Sep. 1990.

(56) References Cited

OTHER PUBLICATIONS

Tiziani et al., "Metabolomic Profiling of Drug Response in Acute Myeloid Leukaemia Cell lines," PLoS One, vol. 4, Issue 1, e4251, Jan. 22, 2009.

* cited by examiner

PASSIVE REPLACEMENT OF MEDIA

CROSS-REFERENCE TO RELATED APPLICATION

This application claims the benefit of U.S. Provisional Application Ser. No. 61/970,274, filed on Mar. 25, 2014, and entitled, "Passive Replacement of Media." The disclosure of the above-identified application is hereby incorporated by reference in its entirety as if set forth herein in full for all that it teaches and for all purposes.

BACKGROUND

Cell Expansion Systems (CESs) are used to expand and differentiate cells. Cell expansion systems may be used to expand, e.g., grow, stem cells, such as mesenchymal stem cells, human mesenchymal stem cells, etc. Cell expansion systems may also expand other types of cells, such as bone marrow cells, for example. Stem cells which are expanded from donor cells may be used to repair or replace damaged or defective tissues and have broad clinical applications for a wide range of diseases. Cells, of both adherent and non-adherent type, may be grown in a bioreactor in a cell expansion system.

SUMMARY

Embodiments of the present disclosure generally relate to using the passive replacement of media in a cell expansion system to conserve media and provide an environment conducive to encouraging cell growth. The expansion of cells, such as human mesenchymal stem cells, for example, uses external chemical signaling between the cells to initiate cell expansion by inhibiting lag phase signaling pathways internal to the cells. The expansion of other types of cells, such as Chinese hamster ovary (CHO) cells, for example, may be particularly sensitive to chemical signaling between the cells, according to embodiments. For example, CHO cells secrete cholecystokinin (CCK), a regulatory hormone responsible in part for cell culture maintenance and proliferation via chemical signaling. In embodiments, CCK may be small enough to pass through the microporous membrane of a hollow fiber bioreactor. Due to such ability to pass through the membrane, dilution of chemical signaling may occur regardless of inlet media addition to the intracapillary or extracapillary loop of a cell expansion system. To reduce or prevent the dilution of external chemical signaling in a closed, automated cell expansion system and, thus, reduce the lag phase of the cells, aspects of particular embodiments provide for passively replacing media by interrupting protocol procedures being executed and replacing a waste or outlet bag(s) used with the cell expansion system with a media bag(s). In embodiments, a bag containing base media may be attached to a waste line of the cell expansion system, in which such configuration allows base media to be added to the system at the rate of evaporation during conditions of no active inlet fluid flow. In embodiments, other types of replacement fluids are used in the media bag(s), such as, for example, complete media or cytokines or other cell-signaling protein molecules. In other embodiments, fluid may be passively replaced by interrupting protocol procedures being executed and allowing any fluid in the waste or outlet bag (assuming no constituents toxic to cell growth are present in the waste or outlet bag) to be passively added to the system at the rate of evaporation during conditions of no active inlet fluid flow. The passive addition of fluid avoids adding an excess amount of fluid, in which an excess amount of fluid may dilute the chemical signaling used to initiate cell expansion. Further, media constituents themselves may ultimately be conserved, resulting in increased system efficiencies and a savings of resources.

Embodiments of the present disclosure further relate to enhancing chemical signaling by adding a molecule(s), e.g. cell-signaling protein molecules, such as cytokines, according to embodiments, to the expanding cell population in a bioreactor. In an embodiment, cytokines, or other type of cell-signaling protein molecules, may be added to the bioreactor by, for example, welding a tubing line or other material connected to a cytokine source, or pre-filled with cytokines or other desired constituents, to a sampling coil or sample coil of the cell expansion system. The cytokines may thus be added to the bioreactor at the sample coil. Such direct addition results in a significant savings of cytokines, which may be costly, because a much higher amount of cytokines would need to be added to a media bag to compensate for dilution of the cytokines by the media than are needed when only the cytokine source itself replenishes the bioreactor. Further, cytokines tend to degrade quickly over time or with exposure to ultra-violet (UV) light, in which such degradation may be minimized by adding cytokines closer to the expanding cell population, e.g., at the sample coil of the bioreactor itself which is isolated from UV light sources. In such embodiments, the cytokines in the bioreactor may thus be maintained at a certain level while conserving resources.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" may mean A alone, B alone, C alone, A and B together, A and C together, B and C together, or A, B and C together.

This Summary is included to provide a selection of concepts in a simplified form, in which such concepts are further described below in the Detailed Description. This Summary is not intended to be used in any way to limit the claimed subject matter's scope. Features, including equivalents and variations thereof, may be included in addition to those provided herein.

BRIEF DESCRIPTION OF THE DRAWINGS

Embodiments of the present disclosure may be described by referencing the accompanying figures. In the figures, like numerals refer to like items.

DETAILED DESCRIPTION

Figure 1:
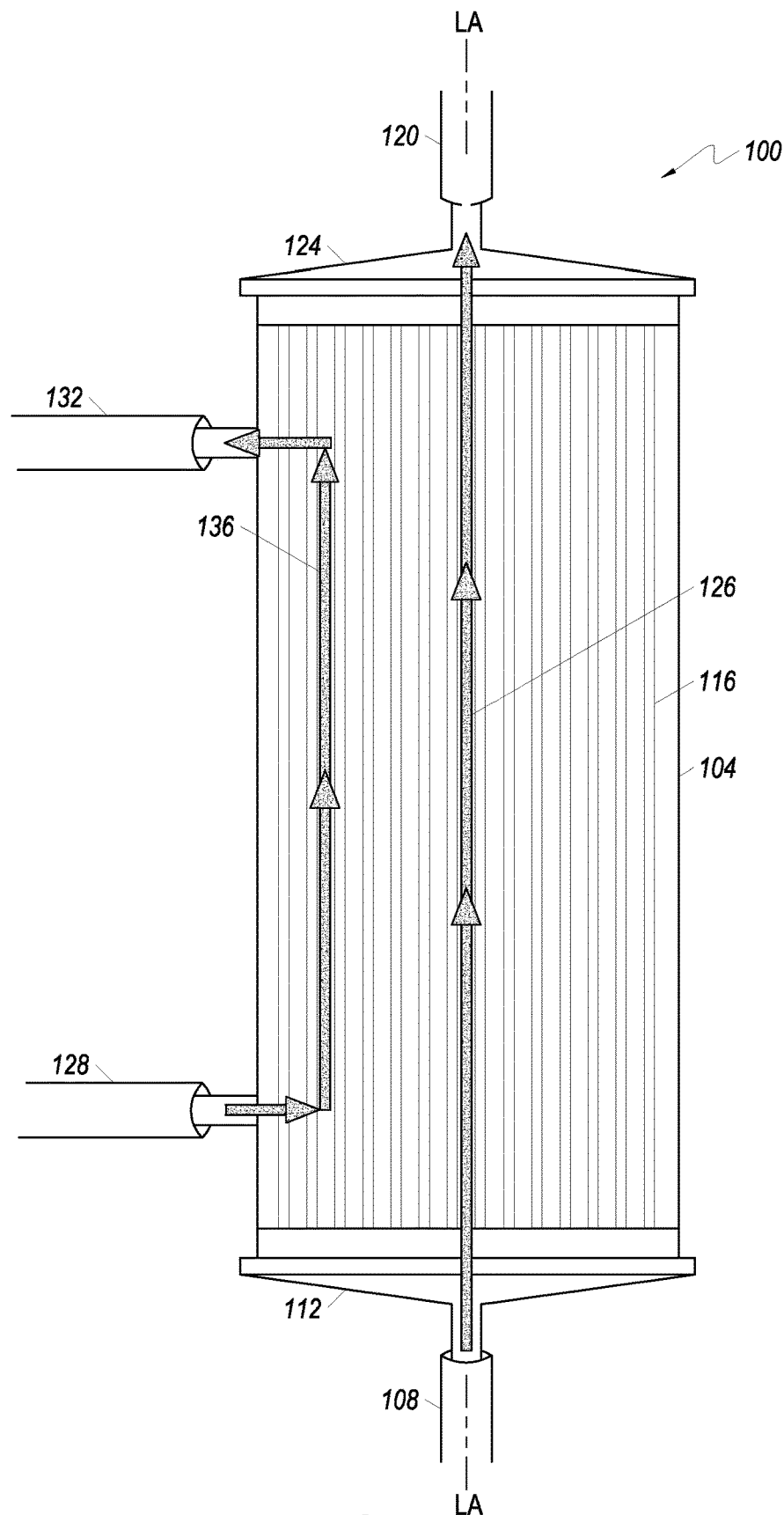
FIG. 1 depicts a perspective view of a hollow fiber bioreactor, in accordance with embodiments of the present disclosure.

The following Detailed Description provides a discussion of illustrative embodiments with reference to the accompanying drawings. The inclusion of specific embodiments herein should not be construed as limiting or restricting the present disclosure. Further, while language specific to features, acts, and/or structures, for example, may be used in describing embodiments herein, the claims are not limited to the features, acts, and/or structures described. A person of skill in the art will appreciate that other embodiments, including improvements, are within the spirit and scope of the present disclosure.

Embodiments of the present disclosure are generally directed to systems and methods for passively replacing media in a cell expansion system. Passive replacement of media may be accomplished by interrupting one or more protocol procedures being executed with respect to the system, e.g., cell loading, cell feeding, etc., and replacing a waste or outlet bag(s) used with the system with a media bag(s). By interrupting, or stopping, mechanisms of the cell expansion system from operating according to the protocol being executed, active inlet fluid flow to the system may be halted to reduce or prevent the dilution of chemical signaling used to inhibit the internal signaling pathways that keep a cell population in the lag phase in a bioreactor of the closed system. Reducing or preventing such dilution may thus reduce the lag phase of cell growth. More efficient and increased cell expansion may therefore occur, in which a greater number of cells may be expanded in a shorter amount of time, according to embodiments of the present disclosure.

Dilution of chemical signaling may occur where an inlet fluid flow into a cell expansion system overcompensates for the evaporation of fluid from the system. For example, an oxygenator or gas transfer module may be used in a closed cell expansion system to maintain the media in fibers in the bioreactor with a desired gas concentration, e.g., 5% $CO_2$, 20% $O_2$, 75% $N_2$. As an example, evaporation in the gas transfer module may occur at 14 mL/day. Without any inlet flow, such evaporation could result in either a build-up of air in the system or a back-flow of fluid from the waste or outlet line in embodiments where the waste line is the only source of fluid for the system which is not occluded by a pump, for example. Using an inlet flow, however, to account for such evaporation may result in overcompensating for the actual amount of fluid lost due to evaporation. For example, in an embodiment, the inlet flow rate into the cell expansion system may have a minimum flow rate. As an example, the inlet flow rate may be set at a minimum rate of 0.1 mL/min or 144 mL/day. Where evaporation in the gas transfer module occurs at 14 mL/day, the fluid lost due to evaporation may be overcompensated for by a rate of 130 mL/day in such embodiment. Such excess 130 mL/day dilutes chemical signaling for initiating cell expansion. For example, such dilution may occur in embodiments where chemical signaling molecules are able to cross, or pass through, a hollow fiber membrane from an intracapillary to an extracapillary side. As a result, adding replacement fluid to either the intracapillary or extracapillary side may result in dilution of the chemical signaling molecules by preventing or reducing them from building up by continuously adding fluid into the system. Where such dilution occurs, communication between the chemical signaling cells may be significantly impacted such that the cells may be unable to expand or even survive. Such dilution may have a particularly significant impact with respect to some cell types as compared to others. For example, reducing or preventing the dilution of chemical signaling molecules may have a significant impact on the expansion of Chinese hamster ovary (CHO) cells, according to embodiments.

In embodiments, instead of using an active inlet fluid flow which may unduly overcompensate for the evaporation of fluid from the system, the active inlet fluid flow to the system may be halted to prevent or minimize the dilution of chemical signaling used to inhibit the signaling pathways that maintain the cell population in a bioreactor in the lag phase. Such active inlet fluid flow may be halted, for example, by interrupting, or stopping, system mechanisms from operating according to the protocol(s) being executed. Instead of using an overcompensating active inlet fluid flow, such active inlet fluid flow may therefore be stopped while using a passive replacement of media and, therefore, not result in a build-up of air or back-flow of waste. To accomplish such passive media replacement, fluid, e.g., base media, may be added to the system at a rate equal to the rate of evaporation from the system, e.g., such as the rate of evaporation from a gas transfer module, through the use of one or more media bags used to replace one or more waste or outlet bags normally used with the system. The active inlet fluid flow may therefore be stopped while media from the replacement, or substitute, media bag replaces any fluid lost from the system due to evaporation. Such passive addition of fluid avoids adding an excess amount of fluid, in which an excess amount of fluid may dilute the chemical signaling used to initiate cell expansion. As a result, lost fluid may be replaced by adding media at about the rate of evaporation and without diluting chemical signaling used to inhibit signaling pathways that keep the cell population in the lag phase. The lag phase of cell growth may therefore be significantly reduced. Further, media constituents themselves may ultimately be conserved, resulting in increased system efficiencies and a savings of resources.

In other embodiments, fluid may be passively replaced by interrupting protocol procedures being executed and allowing any fluid in the waste or outlet bag (assuming no constituents toxic to cell growth are present in the waste or outlet bag) to be passively added to the system at the rate of evaporation during conditions of no active inlet fluid flow.

The dilution of chemical signaling may be particularly costly where the cell media includes expensive additives. For example, cell-signaling proteins, e.g., cytokines, may be used in the bioreactor to spur cell growth. Diluting cytokines may thus result in significant costs. Accordingly, saving the excess media, e.g., 130 mL/day, may provide significant cost savings over other cell expansion processes. Instead of using an overcompensating active inlet fluid flow, the passive replacement of media may thus be used, according to embodiments of the present disclosure, to maintain media constituent concentrations and conserve media in general. Further, in embodiments, other types of replacement fluids are used in the media bag(s), such as, for example, a media bag comprising cytokines or other cell-signaling protein molecules.

In embodiments, molecules, such as cell-signaling protein molecules, may be added to the bioreactor from a source of such molecules. For example, tubing or other material connected to a molecule source, such as a cytokine source, may be sterile-welded to a sample coil in the cell expansion system, and cytokines in the bioreactor may be replenished by such direct source of cytokines. In an embodiment, such tubing or other material comprises an additional volume added to the sampling coil. In another embodiment, such tubing or other material comprises a segment of tubing or other material used to replace a corresponding segment, or portion, of the sampling coil. In embodiments, such tubing or other material may be pre-filled with the desired constituents, e.g., cytokines. In another embodiment, such tubing or material may be connected to a container or bag comprising such desired constituents. A source of cytokines conserves the amount of cytokines used because the cytokines are not added to an IC media bag, for example, which could dilute the cytokines and use a larger amount of cytokines to achieve the same replenishment concentrations. Further, the cytokines may be added closer to the expanding cell population to minimize degradation of the cytokines. Degradation of the cytokines increases with exposure time to the media bags and UV light where they may be stored. Where cytokines are added closer to the expanding cell population, such degradation may be reduced because the cytokines reach the expanding cell population in a shorter amount of time in an environment protected from any sources of UV light. Such cytokines may be passively or actively added to the bioreactor, according to embodiments, to enhance chemical signaling capabilities. For example, such passive addition of cytokines may occur where the cytokines are added to the system from a media bag used to replace a waste bag, according to an embodiment, at the rate of evaporation during conditions of no active inlet fluid flow.

In an embodiment, chemical signaling may thus be controlled by the addition of cytokines at the sample coil. In another embodiment, chemical signaling may be controlled through such addition of cytokines at the sample coil coupled with the replacement of a waste bag(s) with a media bag(s). By replacing a waste bag(s) with a media bag(s), dilution in the bioreactor may be significantly reduced, as discussed above. Such dilution may be particularly costly where cytokines are used in the cell population expansion in the bioreactor. Preventing or reducing such dilution through the use of the media bag replacement thus may result in significant savings, according to embodiments.

In embodiments, a method provides for controlling chemical signaling in a bioreactor of a closed cell expansion system that includes a disposable tubing set(s). In such embodiments, the method may include the steps of coating the bioreactor and loading cells from a cell inlet bag into the bioreactor. For example, steps for loading cells with circulating distribution may be performed, according to an embodiment. In another embodiment, steps involving the loading of cells with uniform suspension, for example, may be performed. The cells may then be distributed across a membrane of the bioreactor by activating an intracapillary circulation pump, for example. In embodiments, after the loading and the distributing, a waste bag attached to the cell expansion system may be replaced with a media bag. After the waste bag is replaced, one or more pumps, e.g., an intracapillary circulation pump, extracapillary inlet pump, and intracapillary inlet pump, may be turned "OFF" or otherwise deactivated, according to an embodiment. In another embodiment, one or more pumps may be turned "OFF" or otherwise deactivated before replacing the outlet or waste bag. For example, in an embodiment expanding adherent cells, the intracapillary circulation pump may be deactivated after replacing a waste or outlet bag with a media bag. In another embodiment expanding adherent cells, for example, the intracapillary circulation pump may be deactivated before replacing the waste or outlet bag with a media bag. In yet other embodiments expanding non-adherent cells, for example, the intracapillary circulation pump may stay activated while one or more other pumps are deactivated.

In at least one embodiment, the media from the media bag flows through an extracapillary waste valve to the extracapillary circulation loop to replenish fluid evaporated from a gas transfer module in the extracapillary circulation loop. In embodiments, after replacement of the waste bag with the media bag, the method further includes deactivating an intracapillary inlet pump, deactivating an extracapillary inlet pump, maintaining an extracapillary circulation pump in an activated state, and maintaining the extracapillary waste valve in an open position.

In some embodiments, the cells include adherent cells, and the method may include the additional steps of enabling the adherent cells to attach to the bioreactor membrane and maintaining flow on an extracapillary circulation loop by maintaining an extracapillary circulation pump in an activated state. In some embodiments, the adherent cells are allowed to attach to the bioreactor membrane for a period of time, e.g., a first period of time, of about eighteen (18) hours to about twenty-four (24) hours. In other embodiments, the cells include non-adherent or suspension cells, such as, for example, CHO cells.

The method, in some embodiments, may further include feeding the cells in the bioreactor of the closed cell expansion system while maintaining the media bag in replacement of the waste bag and while reducing an intracapillary inlet rate. In these embodiments, feeding may include activating the intracapillary circulation pump. In embodiments, the feeding of the cells may be stopped after a second period of time of about forty-five (45) hours to about fifty (50) hours of feeding. In yet other embodiments, the feeding may be stopped after a second period of time of about forty-eight (48) hours of feeding.

The method, in embodiments, further involves measuring a concentration of lactate generated from the cells and stopping the feeding of the cells when the concentration of lactate is equal to or greater than about 6 mmol/L. In some embodiments, the method includes removing the media bag, inserting the waste bag, activating the intracapillary inlet pump, activating the intracapillary circulation pump, and maintaining an extracapillary circulation pump in an activated state. The intracapillary inlet pump may operate at an intracapillary inlet rate of about 0.1 mL/min, in some embodiments. The intracapillary circulation pump may operate at an intracapillary circulation rate of about 20 mL/min, in some embodiments. The extracapillary circulation pump may operate at an extracapillary circulation rate of about 30 mL/min, according to embodiments. In an embodiment, the method may additionally involve doubling, or otherwise increasing, according to other embodiments, the intracapillary inlet rate until a desired number of the cells are available for harvest. When the desired number of cells is available for harvest, embodiments include the additional steps of: releasing the cells from the membrane of the bioreactor, suspending the cells in the intracapillary circulation loop, and transferring the cells in suspension to a harvest bag.

Steps performed, including, for example, coating the bioreactor, loading cells, and distributing the cells, may be performed automatically in some embodiments, such as by a processor executing pre-programmed tasks stored in memory. Replacing a waste bag with a media bag may be performed manually in some embodiments and automatically in others. The automatic replacement of the waste bag may include, in embodiments, receiving, by a processor, a command to execute a task for replacing the waste bag, the task being stored in a memory. In an embodiment, for example, upon receiving such a command for the bag replacement, a processor may send a signal to close a valve(s), for example, for the waste bag and open another valve(s) for an attached media bag. In another embodiment, a single valve, or other type of mechanism, may control the flow of fluid from the waste bag or attached media bag.

The media bag may store base media and, in some embodiments, stores about 500 mL of base media, for example. The base media may include a number of different components, including, for example, glucose to provide an energy source for cells to grow, according to an embodiment. The media bag may comprise other fluids and/or constituents in accordance with embodiments of the present disclosure.

Other embodiments of the method provide for additional steps, some of which include loading cell-signaling protein molecules into a sample coil of an intracapillary circulation loop and activating the intracapillary circulation pump to transfer the cell-signaling protein molecules to the bioreactor. In some embodiments, the sample coil and the intracapillary circulation loop are part of a disposable tubing set.

In embodiments, the method may further include, prior to loading cells into the bioreactor, replacing fluid on an intracapillary circulation loop and on an extracapillary circulation loop with media from an intracapillary media bag, and allowing the media from the intracapillary media bag to reach equilibrium with a gas supply.

Some embodiments are directed to a cell expansion system, as noted above. In embodiments, such cell expansion system is closed, in which a closed cell expansion system comprises contents that are not directly exposed to the atmosphere. Such cell expansion system may be automated. In embodiments, cells, of both adherent and non-adherent type, may be grown in a bioreactor in the cell expansion system. According to embodiments, the cell expansion system may include base media. Methods for replenishment of media are provided for cell growth occurring in a bioreactor of the closed cell expansion system. In embodiments, the bioreactor used with such systems may be a hollow fiber bioreactor. Many types of bioreactors may be used in accordance with embodiments of the present disclosure.

The system may include, in embodiments, a bioreactor that further includes a first fluid flow path having at least opposing ends, a first opposing end of the first fluid flow path fluidly associated with a first port of a hollow fiber membrane and a second end of the first fluid flow path fluidly associated with a second port of the hollow fiber membrane, wherein the first fluid flow path comprises an intracapillary portion of the hollow fiber membrane. The system may further include a fluid inlet path fluidly associated with the first fluid flow path, wherein the plurality of cells are introduced into the first fluid flow path through a first fluid inlet path. A first pump for circulating fluid in the first fluid flow path of the bioreactor may also be included. In embodiments, the system includes a controller, e.g., first controller, for controlling operation of the first pump. In an embodiment, the controller may be a computing system, including a processor, for example. The controller may be configured, in embodiments, to control the pump to circulate a fluid at a first rate within the first fluid flow path, and, when a waste bag in the cell expansion system is replaced with a media bag, the controller stops the circulation of the fluid within the first fluid flow path after the plurality of the cells are loaded into the bioreactor. In some embodiments, a second pump for transferring intracapillary inlet fluid from an intracapillary media bag to the first fluid flow path and a controller, e.g., second controller, for controlling operation of the second pump are included. The second controller in embodiments controls the second pump to transfer cells from a cell inlet bag to the first fluid flow path, and when a waste bag in the cell expansion system is replaced with a media bag, stop the transfer of the cells from the cell inlet bag after the plurality of the cells are loaded into the bioreactor. Additional controllers, e.g., third controller, fourth controller, fifth controller, sixth controller, etc., may be used in accordance with embodiments. Further, additional pumps, e.g., third pump, fourth pump, fifth pump, sixth pump, etc., may be used in accordance with embodiments of the present disclosure. In addition, while the present disclosure may refer to a media bag, a waste bag, a cell inlet bag, etc., multiple bags, e.g., a first media bag, a second media bag, a third media bag, a first waste bag, a second waste bag, a third waste bag, a first cell inlet bag, a second cell inlet bag, a third cell inlet bag, etc., or other types of containers, may be used in embodiments. In other embodiments, a single media bag, a single waste bag, a single cell inlet bag, etc., may be used.

In embodiments, the system may be controlled by, for example: a processor coupled to the cell expansion system; a display device, in communication with the processor, and operable to display data; and a memory, in communication with and readable by the processor, and containing a series of instructions. In embodiments, when the instructions are executed by the processor, the processor receives an instruction to coat the bioreactor, for example. In response to the instruction to coat the bioreactor, the processor may execute a series of steps to coat the bioreactor and may next receive an instruction to load cells into the bioreactor, for example. In response to the instruction to load cells, the processor may execute a series of steps to load the cells from a cell inlet bag into the bioreactor. After loading the cells into the bioreactor, the processor may receive an instruction to stop an intracapillary inlet pump, an intracapillary circulation pump, and an extracapillary inlet pump, for example. The cell expansion system may be operated to allow media to flow from a media bag through an extracapillary waste valve, wherein the extracapillary waste valve is in an open position. The processor may receive an instruction to pump the media in the extracapillary circulation loop to replace fluid evaporated from a gas transfer module located in the extracapillary circulation loop.

Referring to FIG. 1, an example of a hollow fiber cell growth chamber 100 which may be used with the present disclosure is shown in front side elevation view. Cell growth chamber 100 has a longitudinal axis LA-LA and includes cell growth chamber housing 104. In at least one embodiment, cell growth chamber housing 104 includes four openings or ports: IC inlet port 108, IC outlet port 120, EC inlet port 128, and EC outlet port 132.

According to embodiments of the present disclosure, fluid in a first circulation path enters cell growth chamber 100 through IC inlet port 108 at a first longitudinal end 112 of the cell growth chamber 100, passes into and through the intracapillary side (referred to in various embodiments as the intracapillary ("IC") side or "IC space" of a hollow fiber membrane) of a plurality of hollow fibers 116, and out of cell growth chamber 100 through IC outlet port 120 located at a second longitudinal end 124 of the cell growth chamber 100. The fluid path between the IC inlet port 108 and the IC outlet port 120 defines the IC portion 126 of the cell growth chamber 100. Fluid in a second circulation path flows in the cell growth chamber 100 through EC inlet port 128, comes in contact with the extracapillary side or outside (referred to as the "EC side" or "EC space" of the membrane) of the hollow fibers 116, and exits cell growth chamber 100 via EC outlet port 132. The fluid path between the EC inlet port 128 and the EC outlet port 132 comprises the EC portion 136 of the cell growth chamber 100. Fluid entering cell growth chamber 100 via the EC inlet port 128 may be in contact with the outside of the hollow fibers 116. Small molecules (e.g., ions, water, oxygen, lactate, etc.) may diffuse through the hollow fibers 116 from the interior or IC space of the hollow fiber to the exterior or EC space, or from the EC space to the IC space. Large molecular weight molecules, such as growth factors, are typically too large to pass through the hollow fiber membrane, and remain in the IC space of the hollow fibers 116. The media may be replaced as needed, in embodiments. Media may also be circulated through an oxygenator or gas transfer module to exchange gasses as needed. Cells may be contained within a first circulation path and/or a second circulation path, as described below, and may be on either the IC side and/or EC side of the membrane, according to embodiments.

The material used to make the hollow fiber membrane may be any biocompatible polymeric material which is capable of being made into hollow fibers. One material which may be used is a synthetic polysulfone-based material, according to an embodiment of the present disclosure. In order for the cells to adhere to the surface of the hollow fibers, the surface may be modified in some way, either by coating at least the cell growth surface with a protein such as fibronectin or collagen, or by exposing the surface to radiation. Gamma treating the membrane surface allows for attachment of adherent cells without additionally coating the membrane with fibronectin or the like. Bioreactors made of gamma treated membranes may be reused. Other coatings and/or treatments for cell attachment may be used in accordance with embodiments of the present disclosure.

Figure 2:
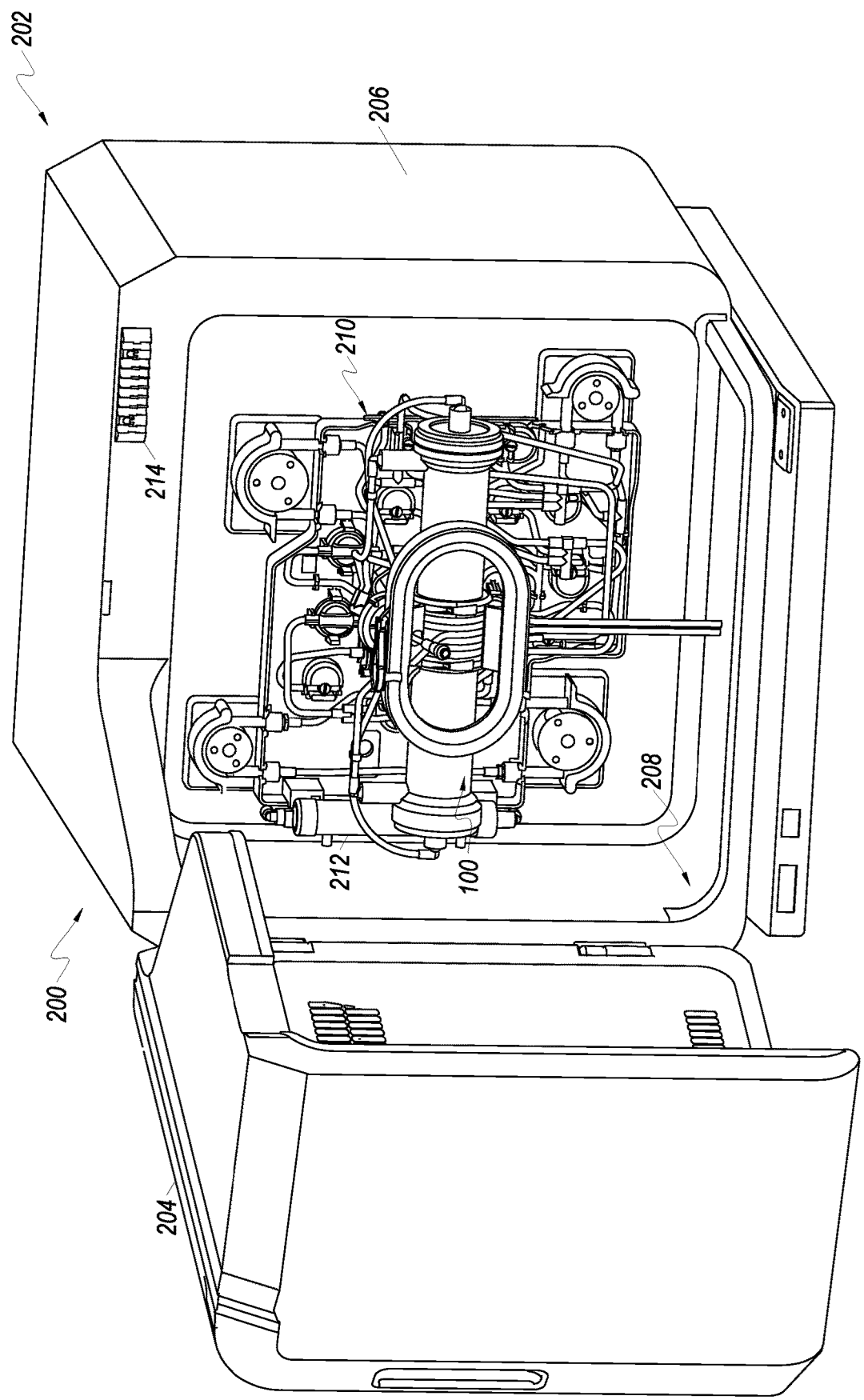
FIG. 2 illustrates a perspective view of a cell expansion system with a premounted fluid conveyance device, in accordance with embodiments of the present disclosure.

Turning to FIG. 2, an embodiment of a cell expansion system 200 with a premounted fluid conveyance assembly is shown in accordance with embodiments of the present disclosure. The CES 200 includes a cell expansion machine 202 that comprises a hatch or closable door 204 for engagement with a back portion 206 of the cell expansion machine 202. An interior space 208 within the cell expansion machine 202 includes features adapted for receiving and engaging a premounted fluid conveyance assembly 210. The premounted fluid conveyance assembly 210 may be detachably-attachable to the cell expansion machine 202 to facilitate relatively quick exchange of a new or unused premounted fluid conveyance assembly 210 at a cell expansion machine 202 for a used premounted fluid conveyance assembly 210 at the same cell expansion machine 202. A single cell expansion machine 202 may be operated to grow or expand a first set of cells using a first premounted fluid conveyance assembly 210 and, thereafter, may be used to grow or expand a second set of cells using a second premounted fluid conveyance assembly 210 without needing to be sanitized between interchanging the first premounted fluid conveyance assembly 210 for the second premounted fluid conveyance assembly 210. The premounted fluid conveyance assembly includes a bioreactor 100 and an oxygenator or gas transfer module 212. Tubing guide slots are shown as 214 for receiving various media tubing connected to premounted fluid conveyance assembly 210, according to embodiments.

Figure 3:
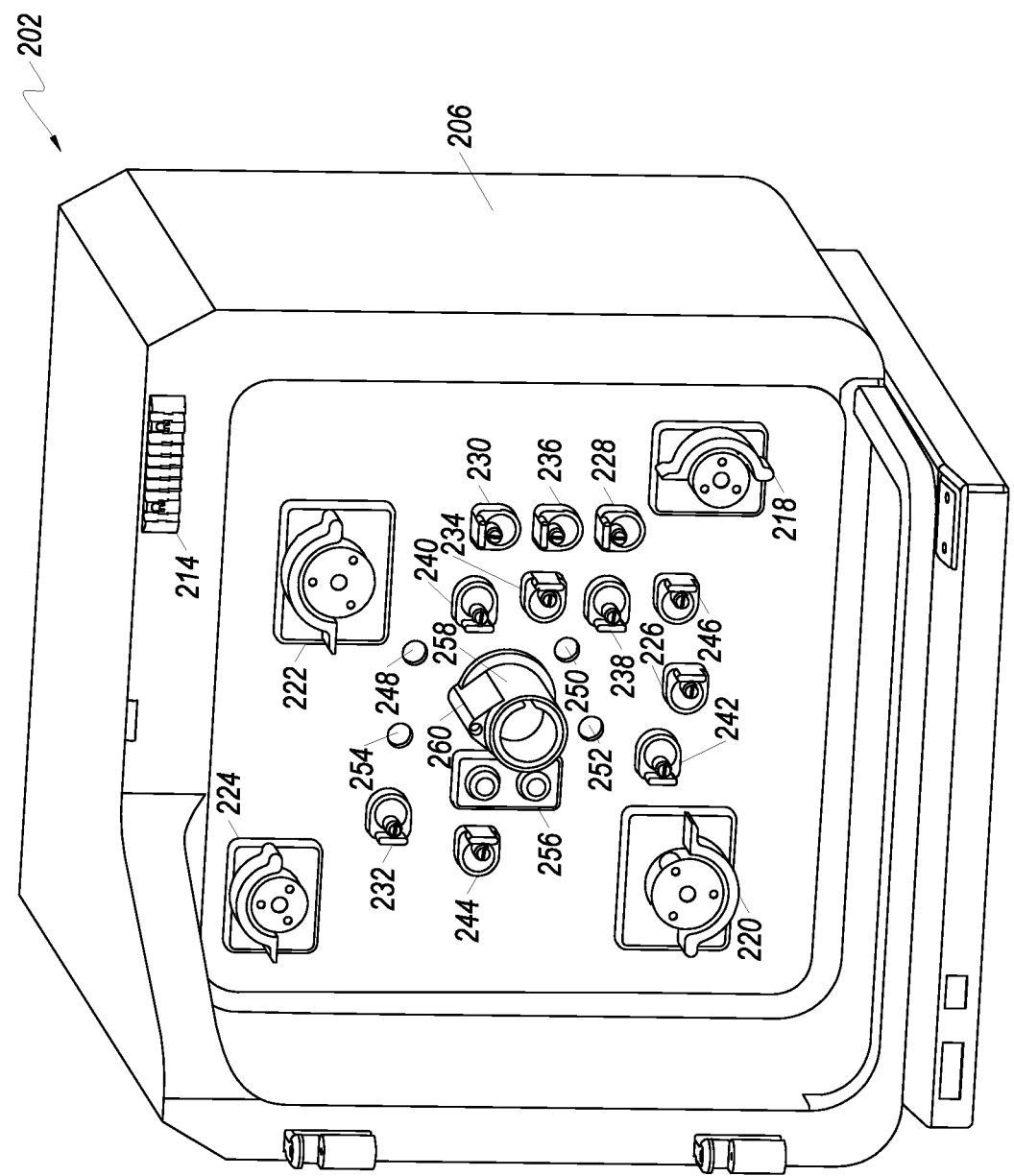
FIG. 3 depicts a perspective view of a housing of a cell expansion system, in accordance with embodiments of the present disclosure.

Next, FIG. 3 illustrates the back portion 206 of cell expansion machine 202 prior to detachably-attaching a premounted fluid conveyance assembly 210 (FIG. 2), in accordance with embodiments of the present disclosure. The closable door 204 (shown in FIG. 2) is omitted from FIG. 3. The back portion 206 of the cell expansion machine 202 includes a number of different structures for working in combination with elements of a premounted fluid conveyance assembly 210. More particularly, the back portion 206 of the cell expansion machine 202 includes a plurality of peristaltic pumps for cooperating with pump loops on the premounted fluid conveyance assembly 210, including the IC circulation pump 218, the EC circulation pump 220, the IC inlet pump 222, and the EC inlet pump 224. In addition, the back portion 206 of the cell expansion machine 202 includes a plurality of valves, including the IC circulation valve 226, the reagent valve 228, the IC media valve 230, the air removal valve 232, the cell inlet valve 234, the wash valve 236, the distribution valve 238, the EC media valve 240, the IC waste valve 242, the EC waste valve 244, and the harvest valve 246. Several sensors are also associated with the back portion 206 of the cell expansion machine 202, including the IC outlet pressure sensor 248, the combination IC inlet pressure and temperature sensors 250, the combination EC inlet pressure and temperature sensors 252, and the EC outlet pressure sensor 254. Also shown is an optical sensor 256 for an air removal chamber.

In accordance with embodiments, a shaft or rocker control 258 for rotating the bioreactor 100 is shown. Shaft fitting 260 associated with the shaft or rocker control 258 allows for proper alignment of a shaft access aperture, see e.g., 424 (FIG. 4) of a tubing-organizer, see e.g., 300 (FIG. 4) of a premounted conveyance assembly 210 or 400 with the back portion 206 of the cell expansion machine 202. Rotation of shaft or rocker control 258 imparts rotational movement to shaft fitting 260 and bioreactor 100. Thus, when an operator or user of the CES 200 attaches a new or unused premounted fluid conveyance assembly 400 (FIG. 4) to the cell expansion machine 202, the alignment is a relatively simple matter of properly orienting the shaft access aperture 424 (FIG. 4) of the premounted fluid conveyance assembly 210 or 400 with the shaft fitting 260.

Figure 4:
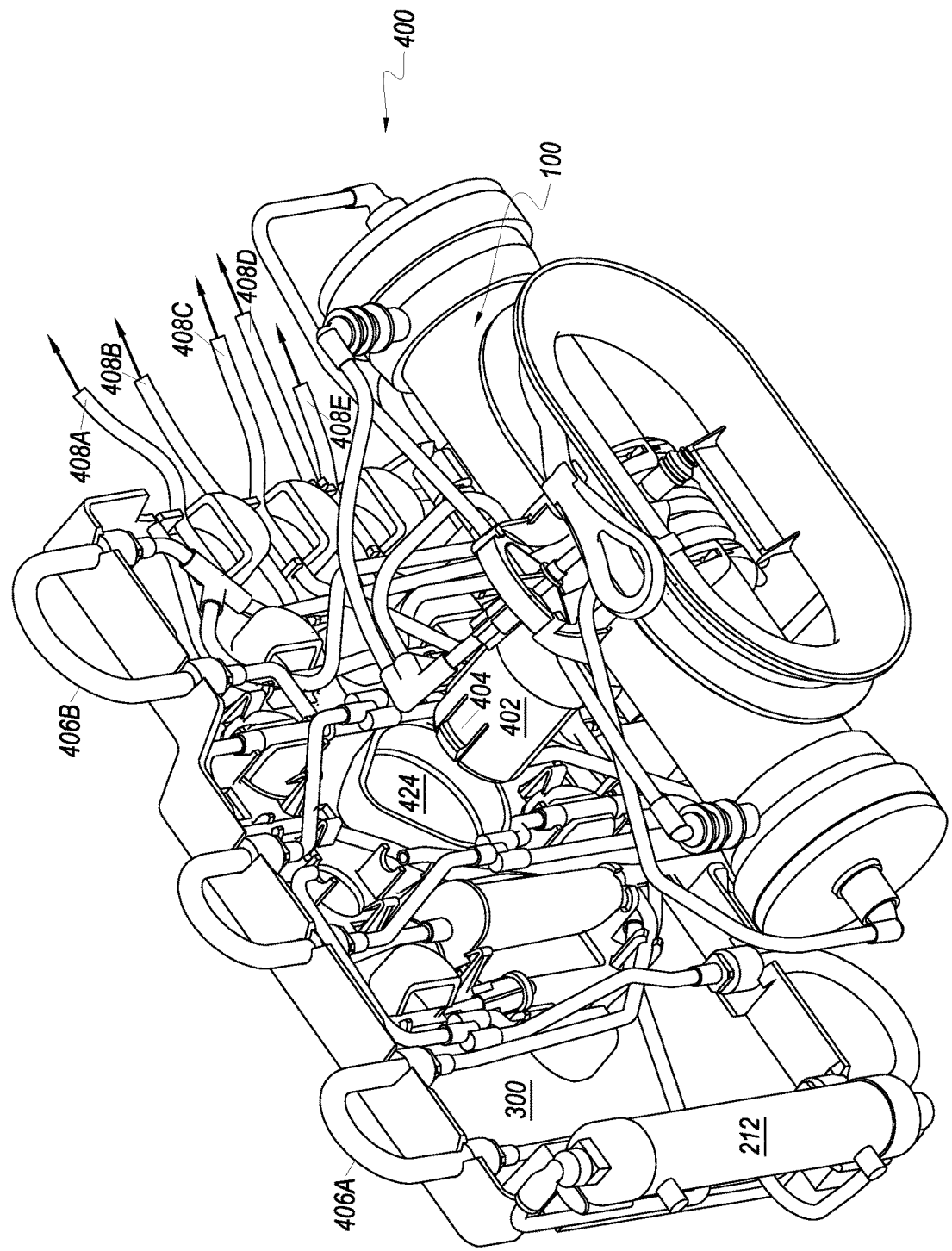
FIG. 4 illustrates a perspective view of a premounted fluid conveyance device, in accordance with embodiments of the present disclosure

Turning to FIG. 4, a perspective view of a detachably-attachable premounted fluid conveyance assembly 400 is shown. The premounted fluid conveyance assembly 400 may be detachably-attachable to the cell expansion machine 202 to facilitate relatively quick exchange of a new or unused premounted fluid conveyance assembly 400 at a cell expansion machine 202 for a used premounted fluid conveyance assembly 400 at the same cell expansion machine 202. As shown in FIG. 4, the bioreactor 100 may be attached to a bioreactor coupling that includes a shaft fitting 402. The shaft fitting 402 includes one or more shaft fastening mechanisms, such as a biased arm or spring member 404 for engaging a shaft, e.g., 258 (shown in FIG. 3), of the cell expansion machine 202.

According to embodiments, the premounted fluid conveyance assembly 400 includes tubing 408A, 408B, 408C, 408D, 408E, etc., and various tubing fittings to provide the fluid paths shown in FIGS. 5-9, as discussed below. Pump loops 406A and 406B are also provided for the pump(s). In embodiments, although the various media may be provided at the site where the cell expansion machine 202 is located, the premounted fluid conveyance assembly 400 may include sufficient tubing length to extend to the exterior of the cell expansion machine 202 and to enable welded connections to tubing associated with the media bags, according to embodiments.

Figure 5:
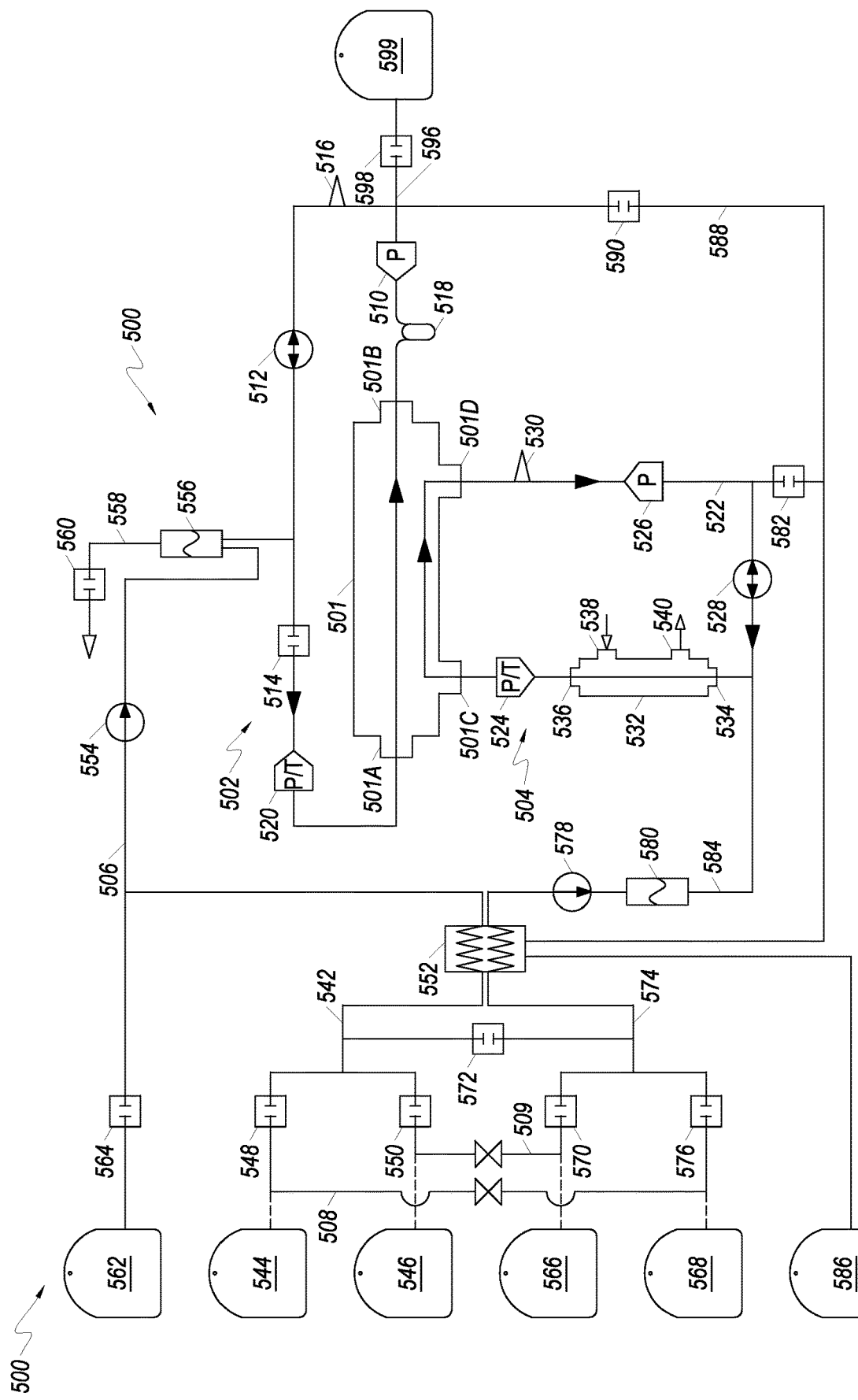
FIG. 5 depicts a schematic of a cell expansion system, in accordance with an embodiment of the present disclosure.
Figure 6:
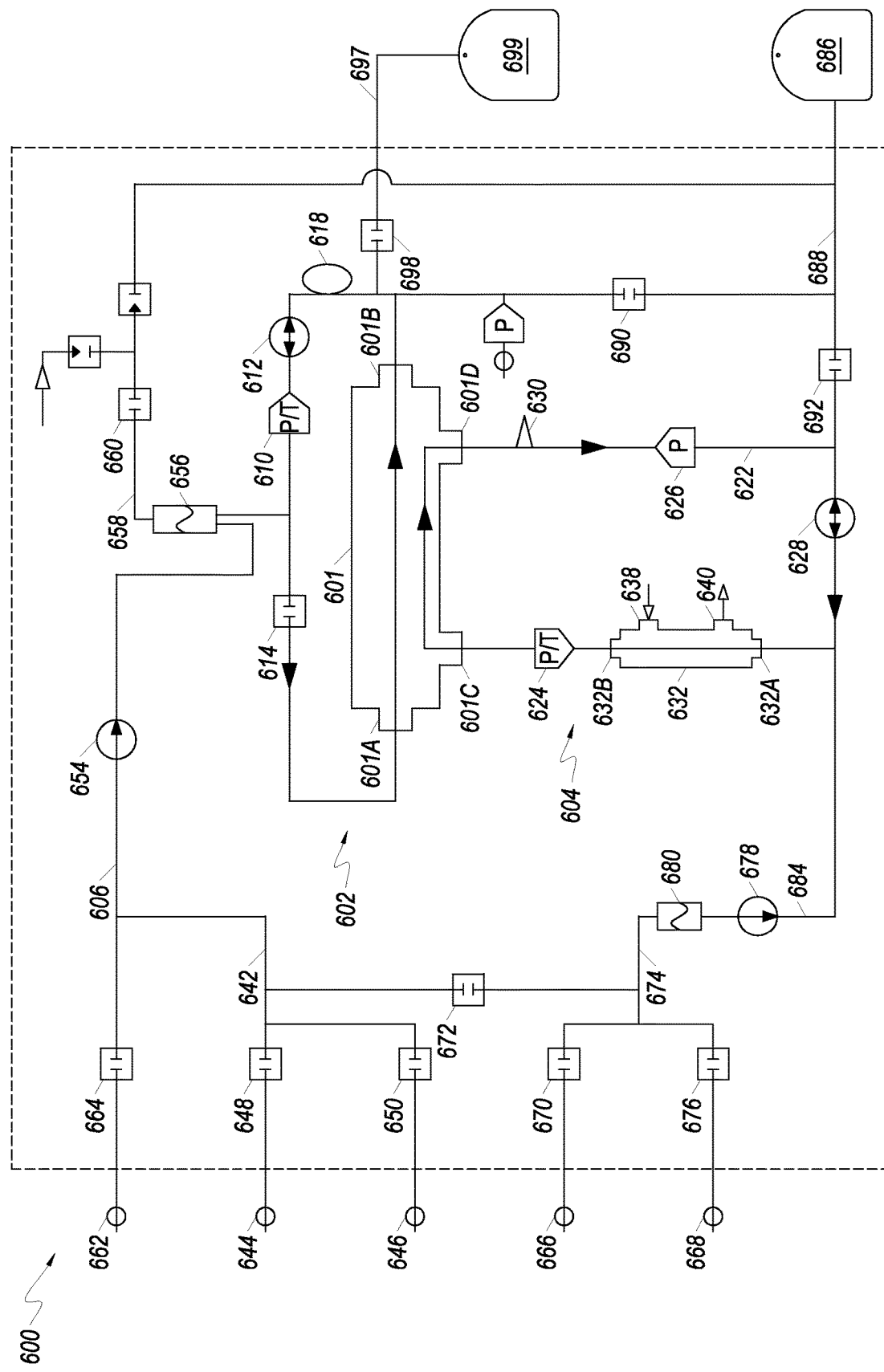
FIG. 6 illustrates a schematic of another embodiment of a cell expansion system.

FIG. 5 illustrates a schematic of an embodiment of a cell expansion system 500, and FIG. 6 illustrates a schematic of another embodiment of a cell expansion system 600. In the embodiments shown in FIGS. 5 and 6, and as described below, the cells are grown in the IC space. However, the disclosure is not limited to such examples and may in other embodiments provide for cells to be grown in the EC space.

FIG. 5 illustrates a CES 500, which includes first fluid circulation path 502 (also referred to as the "intracapillary loop" or "IC loop") and second fluid circulation path 504 (also referred to as the "extracapillary loop" or "EC loop"), according to embodiments. First fluid flow path 506 may be fluidly associated with cell growth chamber 501 to form first fluid circulation path 502. Fluid flows into cell growth chamber 501 through IC inlet port 501A, through hollow fibers in cell growth chamber 501, and exits via IC outlet port 501B. Pressure gauge 510 measures the pressure of media leaving cell growth chamber 501. Media flows through IC circulation pump 512 which may be used to control the rate of media flow. IC circulation pump 512 may pump the fluid in a first direction or second direction opposite the first direction. Exit port 501B may be used as an inlet in the reverse direction. Media entering the IC loop 502 may enter through valve 514. As those skilled in the art will appreciate, additional valves and/or other devices may be placed at various locations to isolate and/or measure characteristics of the media along portions of the fluid paths. Accordingly, it is to be understood that the schematic shown represents one possible configuration for various elements of the CES 500, and modifications to the schematic shown are within the scope of the one or more present embodiments.

With regard to the IC loop 502, samples of media may be obtained from sample port 516 or sample coil 518 during operation. Pressure/temperature gauge 520 disposed in first fluid circulation path 502 allows detection of media pressure and temperature during operation. Media then returns to IC inlet port 501A to complete fluid circulation path 502. Cells grown/expanded in cell growth chamber 501 may be flushed out of cell growth chamber 501 into harvest bag 599 through valve 598 or redistributed within the hollow fibers for further growth. This will be described in more detail below.

Fluid in second fluid circulation path 504 enters cell growth chamber 501 via EC inlet port 501C, and leaves cell growth chamber 501 via EC outlet port 501D. Media in the EC loop 504 may be in contact with the outside of the hollow fibers in the cell growth chamber 501, thereby allowing diffusion of small molecules into and out of the hollow fibers.

Pressure/temperature gauge 524 disposed in the second fluid circulation path 504 allows the pressure and temperature of media to be measured before the media enters the EC space of the cell growth chamber 501. Pressure gauge 526 allows the pressure of media in the second fluid circulation path 504 to be measured after it leaves the cell growth chamber 501. With regard to the EC loop, samples of media may be obtained from sample port 530 or a sample coil during operation.

In embodiments, after leaving EC outlet port 501D of cell growth chamber 501, fluid in second fluid circulation path 504 passes through EC circulation pump 528 to oxygenator or gas transfer module 532. EC circulation pump 528 may also pump the fluid in opposing directions. Second fluid flow path 522 may be fluidly associated with oxygenator or gas transfer module 532 via oxygenator inlet port 534 and oxygenator outlet port 536. In operation, fluid media flows into oxygenator or gas transfer module 532 via oxygenator inlet port 534, and exits oxygenator or gas transfer module 532 via oxygenator outlet port 536. Oxygenator or gas transfer module 532 adds oxygen to and removes bubbles from media in the CES 500. In various embodiments, media in second fluid circulation path 504 may be in equilibrium with gas entering oxygenator or gas transfer module 532. The oxygenator or gas transfer module 532 may be any appropriately sized oxygenator or gas transfer device. Air or gas flows into oxygenator or gas transfer module 532 via filter 538 and out of oxygenator or gas transfer device 532 through filter 540. Filters 538 and 540 reduce or prevent contamination of oxygenator or gas transfer module 532 and associated media. Air or gas purged from the CES 500 during portions of a priming sequence may vent to the atmosphere via the oxygenator or gas transfer module 532.

In the configuration depicted for CES 500, fluid media in first fluid circulation path 502 and second fluid circulation path 504 flows through cell growth chamber 501 in the same direction (a co-current configuration). The CES 500 may also be configured to flow in a counter-current conformation.

In accordance with at least one embodiment, media, including cells (from bag 562), and fluid media from bag 546 may be introduced to first fluid circulation path 502 via first fluid flow path 506. Fluid container 562 (e.g., Cell Inlet Bag or Saline Priming Fluid for priming air out of the system) may be fluidly associated with the first fluid flow path 506 and the first fluid circulation path 502 via valve 564.

Fluid containers, or media bags, 544 (e.g., Reagent) and 546 (e.g., IC Media) may be fluidly associated with either first fluid inlet path 542 via valves 548 and 550, respectively, or second fluid inlet path 574 via valves 570 and 576. First and second sterile sealable input priming paths 508 and 509 are also provided. An air removal chamber (ARC) 556 may be fluidly associated with first circulation path 502. The air removal chamber 556 may include one or more ultrasonic sensors including an upper sensor and lower sensor to detect air, a lack of fluid, and/or a gas/fluid interface, e.g., an air/fluid interface, at certain measuring positions within the air removal chamber 556. For example, ultrasonic sensors may be used near the bottom and/or near the top of the air removal chamber 556 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 500 during portions of the priming sequence or other protocols may vent to the atmosphere out air valve 560 via line 558 that may be fluidly associated with air removal chamber 556.

EC media (from bag 568) or wash solution (from bag 566) may be added to either the first or second fluid flow paths. Fluid container 566 may be fluidly associated with valve 570 that may be fluidly associated with first fluid circulation path 502 via distribution valve 572 and first fluid inlet path 542. Alternatively, fluid container 566 may be fluidly associated with second fluid circulation path 504 via second fluid inlet path 574 and EC inlet path 584 by opening valve 570 and closing distribution valve 572. Likewise, fluid container 568 may be fluidly associated with valve 576 that may be fluidly associated with first fluid circulation path 502 via first fluid inlet path 542 and distribution valve 572. Alternatively, fluid container 568 may be fluidly associated with second fluid inlet path 574 by opening valve 576 and closing valve distribution 572.

An optional heat exchanger 552 may be provided for media reagent or wash solution introduction.

In the IC loop, fluid may be initially advanced by the IC inlet pump 554. In the EC loop, fluid may be initially advanced by the EC inlet pump 578. An air detector 580, such as an ultrasonic sensor, may also be associated with the EC inlet path 584.

In at least one embodiment, first and second fluid circulation paths 502 and 504 are connected to waste line 588. When valve 590 is opened, IC media may flow through waste line 588 and to waste or outlet bag 586. Likewise, when valve 582 is opened, EC media may flow through waste line 588 to waste or outlet bag 586.

In embodiments, cells may be harvested via cell harvest path 596. Here, cells from cell growth chamber 501 may be harvested by pumping the IC media containing the cells through cell harvest path 596 and valve 598 to cell harvest bag 599.

Various components of the CES 500 may be contained or housed within a machine or housing, such as cell expansion machine 202 (FIGS. 2 and 3), wherein the machine maintains cells and media at a predetermined temperature.

Turning to FIG. 6, a schematic of another embodiment of a cell expansion system 600 is shown. CES 600 includes a first fluid circulation path 602 (also referred to as the "intracapillary loop" or "IC loop") and second fluid circulation path 604 (also referred to as the "extracapillary loop" or "EC loop"). First fluid flow path 606 may be fluidly associated with cell growth chamber 601 to form first fluid circulation path 602. Fluid flows into cell growth chamber 601 through IC inlet port 601A, through hollow fibers in cell growth chamber 601, and exits via IC outlet port 601B. Pressure sensor 610 measures the pressure of media leaving cell growth chamber 601. In addition to pressure, sensor 610 may, in embodiments, also be a temperature sensor that detects the media pressure and temperature during operation. Media flows through IC circulation pump 612 which may be used to control the rate of media flow. IC circulation pump 612 may pump the fluid in a first direction or second direction opposite the first direction. Exit port 601B may be used as an inlet in the reverse direction. Media entering the IC loop may enter through valve 614. As those skilled in the art will appreciate, additional valves and/or other devices may be placed at various locations to isolate and/or measure characteristics of the media along portions of the fluid paths. Accordingly, it is to be understood that the schematic shown represents one possible configuration for various elements of the CES 600, and modifications to the schematic shown are within the scope of the one or more present embodiments.

With regard to the IC loop, samples of media may be obtained from sample coil 618 during operation. Media then returns to IC inlet port 601A to complete fluid circulation path 602. Cells grown/expanded in cell growth chamber 601 may be flushed out of cell growth chamber 601 into harvest bag 699 through valve 698 and line 697. Alternatively, when valve 698 is closed, the cells may be redistributed within chamber 601 for further growth.

Fluid in second fluid circulation path 604 enters cell growth chamber 601 via EC inlet port 601C and leaves cell growth chamber 601 via EC outlet port 601D. Media in the EC loop may be in contact with the outside of the hollow fibers in the cell growth chamber 601, thereby allowing diffusion of small molecules into and out of the hollow fibers that may be within chamber 601, according to an embodiment.

Pressure/temperature sensor 624 disposed in the second fluid circulation path 604 allows the pressure and temperature of media to be measured before the media enters the EC space of the cell growth chamber 601. Sensor 626 allows the pressure and/or temperature of media in the second fluid circulation path 604 to be measured after it leaves the cell growth chamber 601. With regard to the EC loop, samples of media may be obtained from sample port 630 or a sample coil during operation.

After leaving EC outlet port 601D of cell growth chamber 601, fluid in second fluid circulation path 604 passes through EC circulation pump 628 to oxygenator or gas transfer module 632. EC circulation pump 628 may also pump the fluid in opposing directions, according to embodiments. Second fluid flow path 622 may be fluidly associated with oxygenator or gas transfer module 632 via an inlet port 632A and an outlet port 632B of oxygenator or gas transfer module 632. In operation, fluid media flows into oxygenator or gas transfer module 632 via inlet port 632A, and exits oxygenator or gas transfer module 632 via outlet port 632B. Oxygenator or gas transfer module 632 adds oxygen to and removes bubbles from media in the CES 600. In various embodiments, media in second fluid circulation path 604 may be in equilibrium with gas entering oxygenator or gas transfer module 632. The oxygenator or gas transfer module 632 may be any appropriately sized device useful for oxygenation or gas transfer. Air or gas flows into oxygenator or gas transfer module 632 via filter 638 and out of oxygenator or gas transfer device 632 through filter 640. Filters 638 and 640 reduce or prevent contamination of oxygenator or gas transfer module 632 and associated media. Air or gas purged from the CES 600 during portions of a priming sequence may vent to the atmosphere via the oxygenator or gas transfer module 632.

In the configuration depicted for CES 600, fluid media in first fluid circulation path 602 and second fluid circulation path 604 flows through cell growth chamber 601 in the same direction (a co-current configuration). The CES 600 may also be configured to flow in a counter-current conformation, according to embodiments.

In accordance with at least one embodiment, media, including cells (from a source such as a cell container, e.g. a bag) may be attached at attachment point 662, and fluid media from a media source may be attached at attachment point 646. The cells and media may be introduced into first fluid circulation path 602 via first fluid flow path 606. Attachment point 662 may be fluidly associated with the first fluid flow path 606 via valve 664, and attachment point 646 may be fluidly associated with the first fluid flow path 606 via valve 650. A reagent source may be fluidly connected to point 644 and be associated with fluid inlet path 642 via valve 648, or second fluid inlet path 674 via valves 648 and 672.

Air removal chamber (ARC) 656 may be fluidly associated with first circulation path 602. The air removal chamber 656 may include one or more sensors including an upper sensor and lower sensor to detect air, a lack of fluid, and/or a gas/fluid interface, e.g., an air/fluid interface, at certain measuring positions within the air removal chamber 656. For example, ultrasonic sensors may be used near the bottom and/or near the top of the air removal chamber 656 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 600 during portions of a priming sequence or other protocol(s) may vent to the atmosphere out air valve 660 via line 658 that may be fluidly associated with air removal chamber 656.

An EC media source may be attached to EC media attachment point 668 and a wash solution source may be attached to wash solution attachment point 666, to add EC media and/or wash solution to either the first or second fluid flow path. Attachment point 666 may be fluidly associated with valve 670 that may be fluidly associated with first fluid circulation path 602 via valve 672 and first fluid inlet path 642. Alternatively, attachment point 666 may be fluidly associated with second fluid circulation path 604 via second fluid inlet path 674 and second fluid flow path 684 by opening valve 670 and closing valve 672. Likewise, attachment point 668 may be fluidly associated with valve 676 that may be fluidly associated with first fluid circulation path 602 via first fluid inlet path 642 and valve 672. Alternatively, fluid container 668 may be fluidly associated with second fluid inlet path 674 by opening valve 676 and closing valve distribution 672.

In the IC loop, fluid may be initially advanced by the IC inlet pump 654. In the EC loop, fluid may be initially advanced by the EC inlet pump 678. An air detector 680, such as an ultrasonic sensor, may also be associated with the EC inlet path 684.

In at least one embodiment, first and second fluid circulation paths 602 and 604 are connected to waste line 688. When valve 690 is opened, IC media may flow through waste line 688 and to waste or outlet bag 686. Likewise, when valve 692 is opened, EC media may flow to waste or outlet bag 686.

After cells have been grown in cell growth chamber 601, they may be harvested via cell harvest path 697. Here, cells from cell growth chamber 601 may be harvested by pumping the IC media containing the cells through cell harvest path 697, with valve 698 open, into cell harvest bag 699.

Various components of the CES 600 may be contained or housed within a machine or housing, such as cell expansion machine 202 (FIGS. 2 and 3), wherein the machine maintains cells and media at a predetermined temperature. It is further noted that, in embodiments, components of CES 600 and CES 500 (FIG. 5) may be combined. In other embodiments, a CES may include fewer or additional components than those shown in FIGS. 5 and 6 and still be within the scope of the present disclosure.

Figure 7:
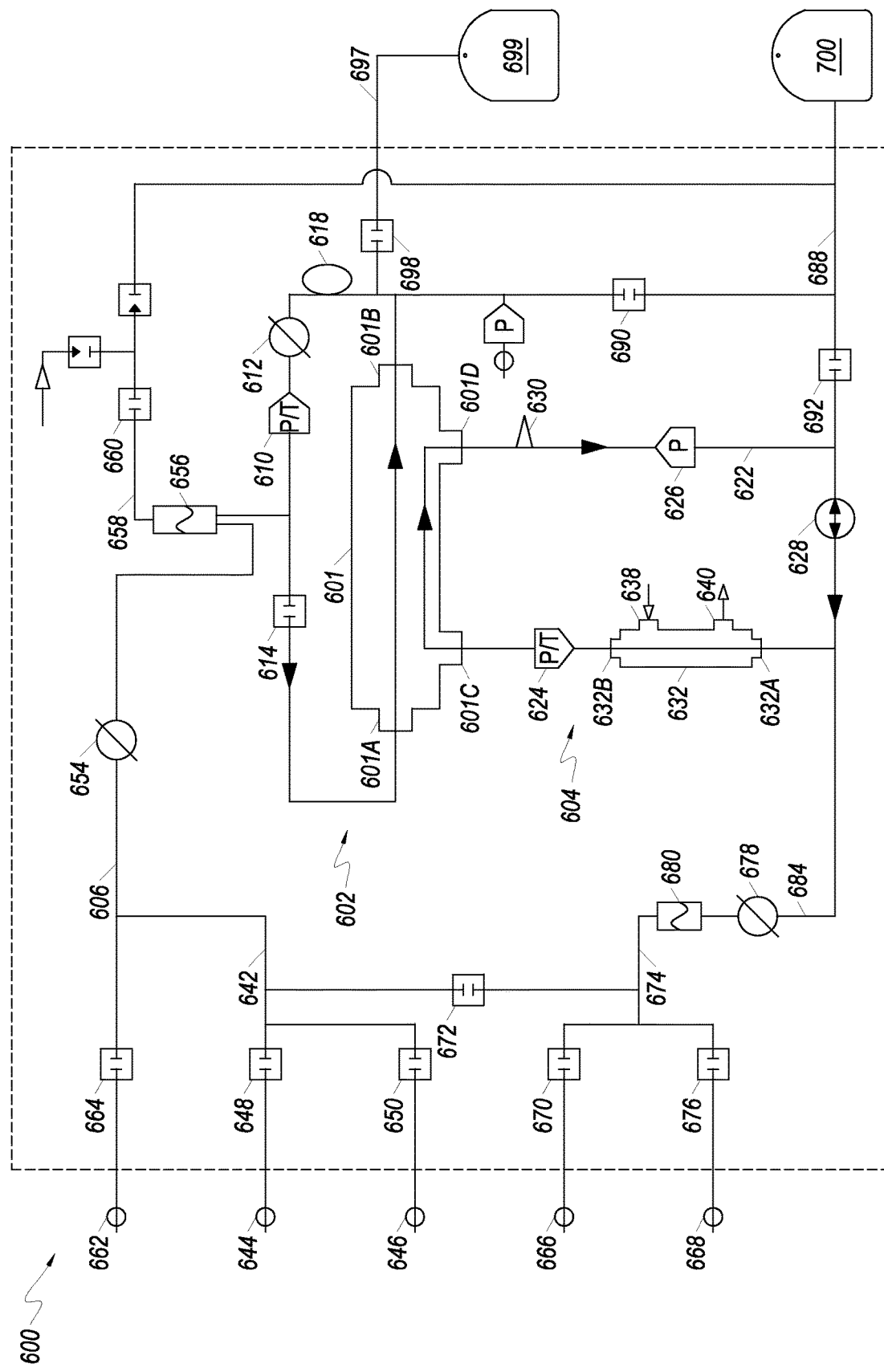
FIG. 7 depicts the cell expansion system embodiment of FIG. 6 with a waste bag replaced by a media bag, in accordance with embodiments of the present disclosure.
Figure 8:
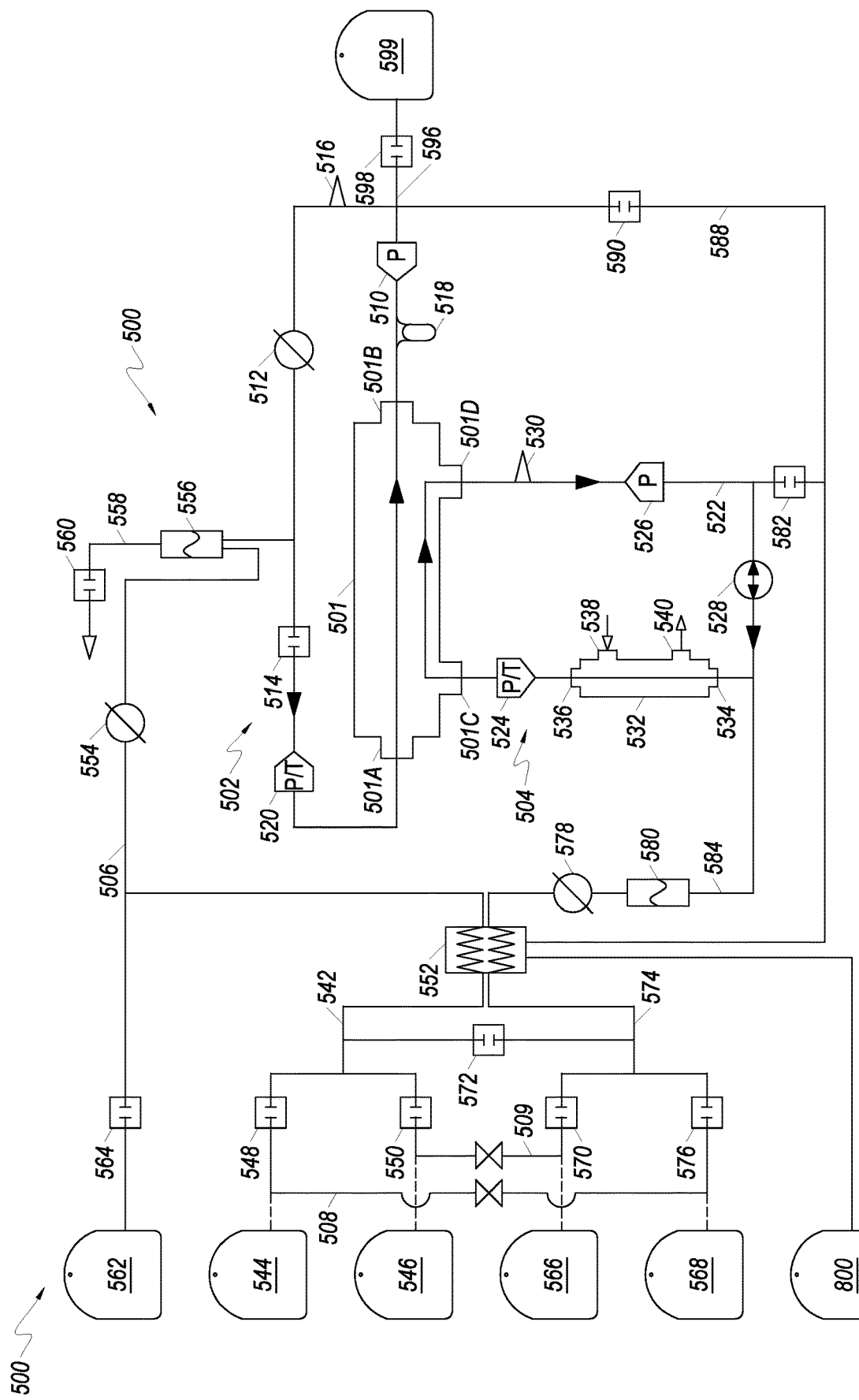
FIG. 8 illustrates the cell expansion system embodiment of FIG. 5 with a waste bag replaced by a media bag, in accordance with embodiments of the present disclosure.

While FIGS. 5 and 6 illustrate schematics of different embodiments of cell expansion systems, FIGS. 7 and 8 depict these same cell expansion systems with the waste or outlet bags (586 and 686) replaced by media bags in accordance with embodiments of the present disclosure. For example, as depicted in FIG. 7, waste or outlet bag 686 in CES 600 (FIG. 6) has been replaced by media, e.g., base media, bag 700. Further, one or more pumps, e.g., IC Circulation Pump 612, EC Inlet Pump 678, and IC Inlet Pump 654, have been turned "OFF," according to an embodiment. There is thus no active inlet fluid flow into cell growth chamber 601. To compensate for fluid lost due to evaporation at the oxygenator or gas transfer module 632, the EC Circulation Pump 628 is left "ON" and the EC Waste Valve 692 is left "OPEN." This configuration allows fluid from media bag 700 to backflow into the CES 600 system at a rate equal to the rate of evaporation from the oxygenator or gas transfer module 632. The fluid lost in the system due to evaporation may thus be replaced without diluting chemical signaling occurring in the bioreactor 601 during cell growth therein. In embodiments, the lag phase of cell growth in the bioreactor 601 may therefore be significantly reduced, and more efficient cell expansion may occur. Further, by turning "OFF," or otherwise deactivating, the inlet pump(s), system resources may be conserved because there is no active inlet fluid being unnecessarily introduced into the system. While FIG. 7 shows an embodiment in which the IC Circulation Pump 612, EC Inlet Pump 678, and IC Inlet Pump 654 have been turned "OFF," other embodiments provide for one or more of such pumps, e.g., the IC Circulation Pump 612, for example, to remain "ON" or activated (not shown in FIG. 7). For example, it may be desired in embodiments to continue circulation in the intracapillary side depending on the type of cells, e.g., non-adherent cells, being expanded, according to an embodiment.

In some embodiments, the media bag (e.g., 700) may be positioned at a physically higher level than at least a portion of the EC loop 604 to allow gravity to assist in draining fluid from the media bag into the EC loop 604. In some embodiments, the waste bag 686 (FIG. 6) may be positioned lower than the EC loop 604 to allow gravity to assist in draining waste media into the waste bag 686. According to embodiments, when the media bag 700 replaces the waste bag 686, the substitute or replacement media bag 700 may be positioned physically higher than the original position of the waste bag 686.

Turning to FIG. 8, a similar configuration is shown, in which, for example, waste bag 586 has been replaced by media, e.g., base media, bag 800. Further, one or more pumps, e.g., IC Circulation Pump 512, EC Inlet Pump 578, and IC Inlet Pump 554, have been turned "OFF," according to an embodiment. There is thus no active inlet fluid flow into the bioreactor 501. To compensate for fluid lost due to evaporation at the gas transfer module or oxygenator 532, the EC Circulation Pump 528 may be left "ON," and the EC Waste Valve 582 may be left "OPEN." In embodiments, such configuration allows fluid from the substitute or replacement media bag 800 to backflow into the system at a rate equal to the rate of evaporation from the gas transfer module or oxygenator 532. The fluid lost in the system due to evaporation may thus be replaced without diluting chemical signaling occurring in the bioreactor 501 during cell growth therein. In embodiments, the lag phase of cell growth in the bioreactor 501 may therefore be significantly reduced, and more efficient cell expansion may occur. Further, by turning "OFF" the one or more inlet pumps, system resources may be conserved because there is no active inlet fluid being unnecessarily introduced into the system. While FIG. 8 shows an embodiment in which the IC Circulation Pump 512, EC Inlet Pump 578, and IC Inlet Pump 554 have been turned "OFF," other embodiments provide for one or more of such pumps, such as the IC Circulation Pump 512, for example, to remain "ON" or activated (not shown in FIG. 8). For example, it may be desired in embodiments to continue circulation in the intracapillary side depending on the type of cells, e.g., non-adherent cells, being expanded, according to an embodiment.

In some embodiments, when the waste bag 586 is replaced by the media bag 800, the substitute or replacement media bag may be positioned physically higher than the original position of the waste bag 586 to allow gravity to assist in draining media into the EC loop 504.

The replacement of the waste bag with a media bag allows passive replacement of fluid lost due to evaporation. Such passive replacement of fluid may provide a significant conservation of fluid in cell expansion processes. In processes involving active media replacement, media may be added and circulated in the IC loop during attachment of cells to replace fluid lost due to evaporation. As described above, if media is added at 0.1 ml/min, which may occur in some processes, according to embodiments, this may result in an excess amount (over the amount that has evaporated) of fluid of up to 130 mL/day in the system, for example. Passive addition of fluid with the replacement of the waste bag with a media bag avoids the addition of an excess amount. As can be appreciated, the media may include expensive additives. Saving about 130 mL/day, for example, may provide significant cost savings over other cell expansion processes.

Figure 9:
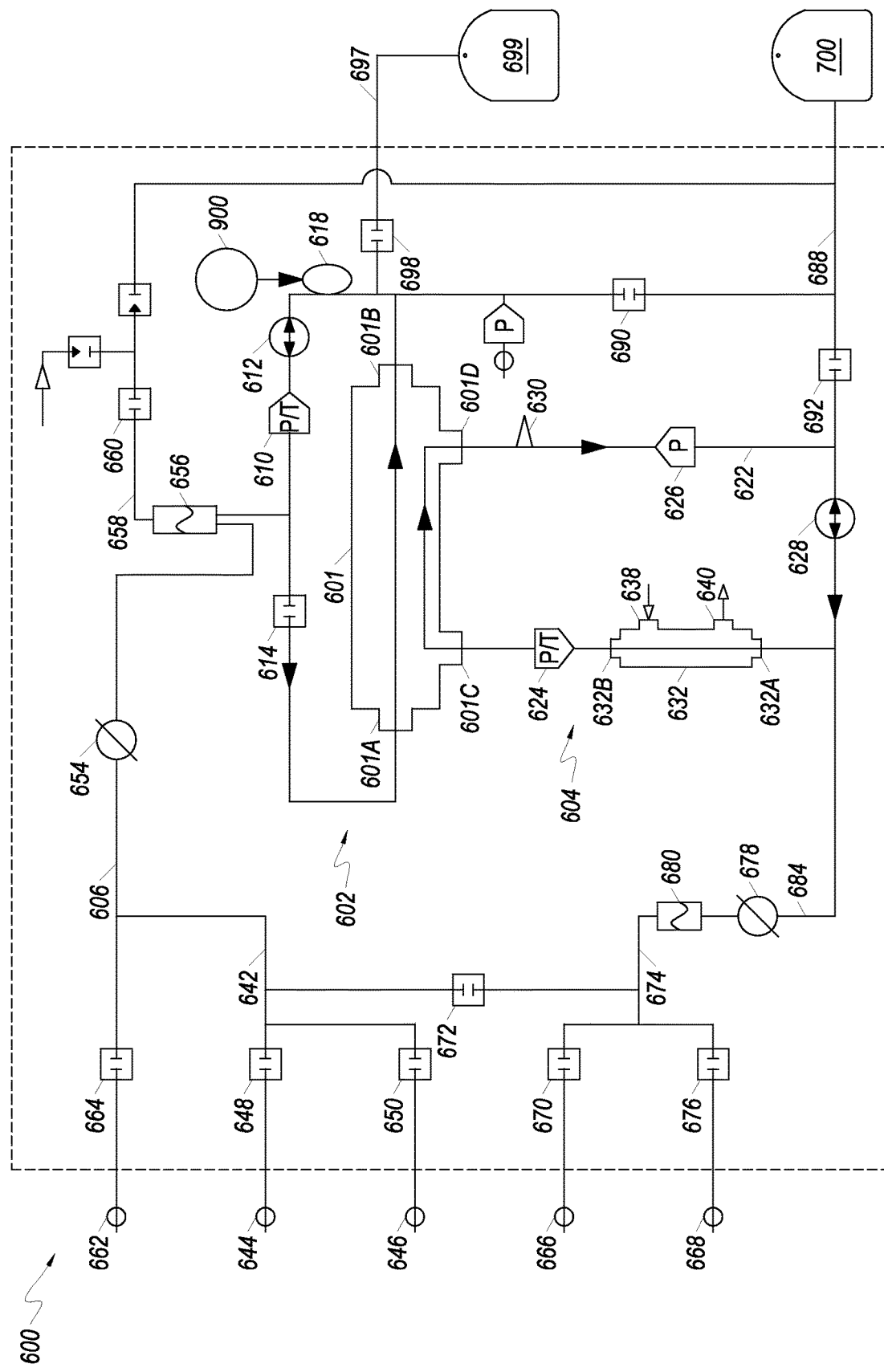
FIG. 9 depicts the cell expansion system embodiment of FIG. 6 with a molecule source included as part of the premounted fluid conveyance device, in accordance with embodiments of the present disclosure.

While FIGS. 7 and 8 allow for the passive replacement of media in a closed cell expansion system through the use of a media bag in replacement of a waste bag, FIG. 9 illustrates an embodiment in which a molecule source, e.g., a cell signaling protein molecule source, may be added to a cell expansion system, such as CES 600 (FIG. 6) (or CES 500 (FIG. 5)), for example. In one embodiment, the molecule source 900 may be a cytokine source welded into the sample coil or sampling coil 618, in which such cytokine source comprises a piece of tubing or other material welded into the sampling coil 618. Through such a source, i.e., direct source, cytokines may be added to the IC loop 602 without diluting such proteins, in which such dilution may occur where the cytokines are added instead at an IC Media bag, for example. In embodiments, the molecules are directly added to the IC loop 602. Such direct addition may also occur at a sample port, for example, according to an embodiment. Cytokines in the cell growth chamber 601 may thus be passively or actively replenished by such cytokine source. In such embodiment, the IC Circulation Pump 612 is turned to the "ON" position to allow the cytokines entering the IC loop 602 at the sampling coil 618 to be pumped to the expanding cell population in the bioreactor 601. Such cell source may ultimately save significant resources where chemical-signaling proteins used in the bioreactor are particularly costly, e.g., cytokines.

Figure 10:
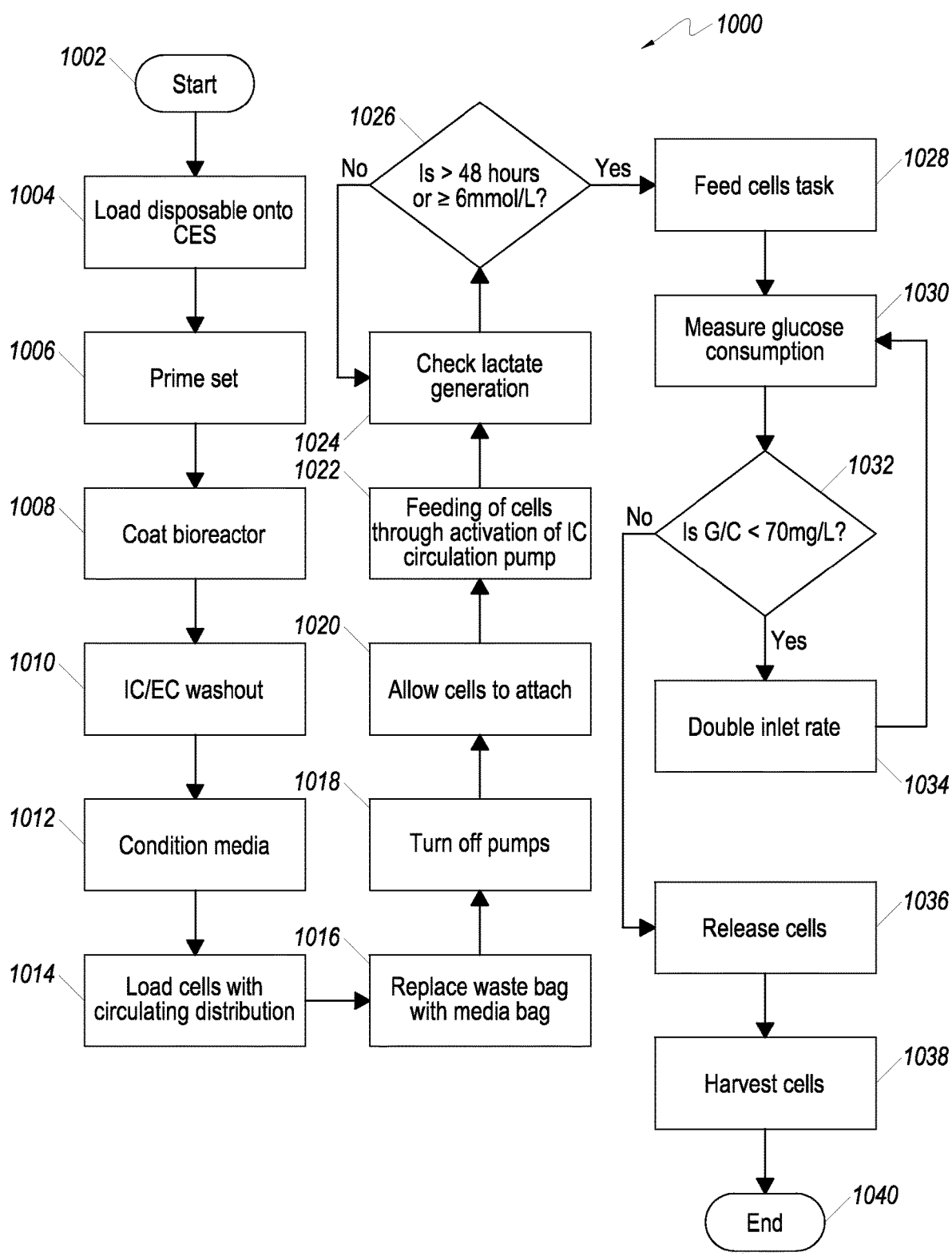
FIG. 10 illustrates a flow diagram depicting the operational characteristics of a process for passively replacing media in a cell expansion system, in accordance with embodiments of the present disclosure.

While various example embodiments of a cell expansion system and methods for passively replacing media in conjunction therewith have been described, FIG. 10 illustrates example operational steps 1000 for passively replacing fluid to control chemical signaling in a closed cell expansion system, in accordance with embodiments of the present disclosure. START operation 1002 is initiated, and process 1000 proceeds to load the disposable tubing set 1004 onto the cell expansion system. Next, the system is primed 1006, such as by having a user or operator instruct the system to prime by selecting a task for priming, for example. In another embodiment, the system is primed 1006 automatically without any selection of a task or instruction from a user or operator. After priming the set, process 1000 proceeds to coat the bioreactor 1008, in which the bioreactor is coated with a reagent. For example, a reagent is loaded into the IC loop until the Reagent Bag is empty. The reagent is chased from the air removal chamber into the IC loop, and the reagent is then circulated in the IC loop. Once the bioreactor is coated, the IC/EC Washout task is executed 1010, in which fluid on the IC circulation loop and on the EC circulation loop is replaced. The replacement volume is determined by the number of IC Volumes and EC Volumes exchanged, according to an embodiment. Next, to maintain the proper or desired gas concentration across fibers in the bioreactor membrane, the condition media task 1012 is executed to allow the media to reach equilibrium with the provided gas supply before cells are loaded into the bioreactor. For example, rapid contact between the media and the gas supply provided by the gas transfer module or oxygenator is provided by using a high EC circulation rate. In an embodiment, the system is then maintained in a proper state until a user or operator is ready to load cells into the bioreactor. In other embodiments, a user or operator may not be needed to perform the noted steps/operations; rather, the steps/operations may be performed automatically by the cell expansion system.

Process 1000 next proceeds to loading cells into the bioreactor from a cell inlet bag with circulating distribution 1014. In an embodiment, cells are loaded into the bioreactor from the cell inlet bag until the bag is empty. Cells are then chased from the air removal chamber to the bioreactor. Larger chase volumes spread the cells and move the cells toward the IC outlet. The distribution of cells is promoted across the membrane via IC circulation, such as through the IC circulation pump, with no IC inlet, for example.

After completion of the load cells with circulating distribution task 1014, the waste or outlet bag is replaced with a media bag 1016. In an embodiment, the media bag comprises about 500 mL of base media. The media bag may comprise other fluids and/or constituents, according to embodiments. In embodiments, the replacement of the outlet or waste bag with a media bag 1016 may be optional, in which fluid may be passively replaced by interrupting protocol procedures being executed and allowing any fluid in the outlet or waste bag (assuming no constituents toxic to cell growth are present in the outlet or waste bag) to be passively added to the system at the rate of evaporation during conditions of no active inlet fluid flow. Such passive addition of fluid avoids adding an excess amount of fluid and, thus, avoids diluting chemical signaling molecules.

Returning to FIG. 10, one or more pumps, e.g., the IC Inlet Pump, the IC Circulation Pump, and the EC Inlet Pump, may then be turned "OFF" or may otherwise be indicated to stop or deactivate 1018. Any adherent cells in the bioreactor are then allowed to attach to the bioreactor membrane 1020 for a period of time, such as for about eighteen (18) to about twenty-four (24) hours, according to an embodiment of the present disclosure. During this timeframe, flow continues on the EC circulation loop, in which the EC circulation rate is maintained at about 30 mL/min, according to an embodiment. A non-zero EC circulation rate helps to maintain the proper or desired gas concentration across the fibers of the bioreactor membrane by continuing to pump fluid in the EC loop through the gas transfer module or oxygenator. While the proper or desired gas concentration is maintained through the use of the gas transfer module, evaporation of fluid also occurs at the gas transfer module. By keeping the EC Waste Valve open, however, media from the media bag (replacing the waste bag) may back-flow into the system and be pumped by the EC Circulation Pump through the EC loop. The media may thus replace fluid lost due to evaporation from the gas transfer module at the rate of evaporation. Thus, membrane fibers in the bioreactor will not be diluted with excess fluid, and the transition of cell growth out of the lag phase will not be inhibited.

After the attaching of any adherent cells for about eighteen (18) to about twenty-four (24) hours, according to an embodiment, a continued cell attachment phase 1022 continues for up to about forty-eight (48) hours. During operation 1022, the IC circulation pump may be activated or turned "ON" to provide even the furthest fibers of the bioreactor membrane with media. For example, the IC circulation pump may be activated to adjust the IC circulation rate to about 20 mL/min, according to an embodiment of the present disclosure. However, during this period of modified feeding through activation of the IC circulation pump 1022, the IC inlet rate remains at 0 mL/min. Rather, the substitute media bag (in replacement of the waste bag) continues to provide any necessary fluid replacement to the system while not diluting the membranes or inhibiting chemical signaling. Operation 1022 with modified feeding of the cells thus allows for cell attachment to continue without disruption of chemical signaling occurring in the bioreactor. This continued cell attachment phase continues, according to embodiments, for up to about forty-eight (48) additional hours and/or, in embodiments, until the lactate generation of the cells is greater than or equal to about 6 mmol/L. In an embodiment, the concentration of lactate is measured. In another embodiment, the lactate generation rate, for example, is measured. In an embodiment, the lactate generation is thus checked at operation 1024 to determine if the concentration of lactate is equal to or exceeds 6 mmol/L. In other embodiments, the lactate generation is checked at operation 1024 to determine the concentration of lactate in relation to another predetermined amount.

Process 1000 next proceeds to query 1026, in which it is determined whether more than forty-eight hours has passed since the IC circulation pump was activated or whether the concentration of lactate is equal to or greater than about 6 mmol/L. If less than forty-eight (48) hours has passed or if the concentration of lactate is not equal to or in excess of about 6 mmol/L, process 1000 proceeds NO to check lactate generation operation 1024 and then to query 1026 again. It is noted that the present disclosure is not limited to determining whether forty-eight (48) hours have passed or whether there is a lactate concentration equal to or in excess of 6 mmol/L. In other embodiments, process 1000 may involve a different predetermined period of time. For example, at query 1026, a determination may be made whether about 12 hours, about 24 hours, about 36 hours, or about 40 hours have passed. In other embodiments, the predetermined period of time may be about 50 hours or about 60 hours. In embodiments, a determination may be made whether more than about 12 hours, more than about 24 hours, more than about 36 hours, or more than about 40 hours have passed. In other embodiments, a determination may be made whether less than about 60 hours or less than about 50 hours have passed. In yet other embodiments, process 1000 may involve determining whether the concentration of lactate is equal to or greater than another predetermined amount, such as about 3 mmol/L, about 4 mmol/L, about 5 mmol/L, about 7 mmol/L, or about 8 mmol/L. In embodiments, a determination may be made whether the concentration of lactate is more than about 3 mmol/L, more than about 4 mmol/L, or more than about 5 mmol/L. In other embodiments, a determination may be made whether the concentration of lactate is less than about 8 mmol/L or less than about 7 mmol/L.

If at query 1026 it is determined that more than about forty-eight (48) hours has passed since the IC circulation pump was activated or that the concentration of lactate is equal to or greater than 6 mmol/L, process 1000 proceeds YES to feed cells operation 1028, in which the IC inlet pump is activated or turned "ON" to maintain an IC Inlet Rate of 0.1 mL/min. Next, process 1000 proceeds to measure the glucose consumption 1030. In an embodiment, the concentration of glucose is measured. In another embodiment, the glucose consumption rate, for example, is measured. At query 1032, it is determined whether the measured glucose consumption is less than about 70 mg/L, in an embodiment. If the glucose consumption is less than about 70 mg/L (or another predetermined amount, according to other embodiments), process 1000 proceeds YES to double the IC Inlet Rate 1034. Process 1000 then proceeds to operation 1030 to continue measuring the glucose consumption of the cells and back to query 1032.

The present disclosure is not limited to determining whether the glucose consumption is less than about 70 mg/L. In other embodiments, process 1000 may involve a different predetermined amount. For example, in embodiments, process 1000 may involve determining whether the glucose consumption is less than another predetermined amount, such as about 65 mg/L, about 60 mg/L, or about 55 mg/L, for example. In other embodiments, the process 1000 may involve determining whether the glucose consumption is less than another predetermined amount, such as about 85 mg/L, about 80 mg/L, or about 75 mg/L, for example. In embodiments, a determination may be made whether the glucose consumption is more than about 55 mg/L, more than about 60 mg/L, or more than about 65 mg/L. In other embodiments, a determination may be made whether the glucose consumption is less than about 85 mg/L, less than about 80 mg/L, or less than about 75 mg/L.

If, at query 1032, the glucose consumption is determined to be greater than 70 mg/L, process 1000 proceeds NO to release the cells operation 1036, in which the cells are released from the membrane of the bioreactor and are suspended in the IC loop. In embodiments, an IC/EC Washout task in preparation for adding a reagent is performed. For example, IC/EC media may be replaced with a phosphate buffered saline (PBS) to remove protein, calcium ($Ca^{2+}$), and magnesium ($Mg^{2+}$) in preparation for adding trypsin, or another chemical-releasing agent, to release any adherent cells. A reagent may be loaded into the system until the reagent bag is empty. The reagent may be chased into the IC loop, and the reagent may be mixed within the IC loop. Following the release of any adherent cells, harvest operation 1038 transfers the cells in suspension from the IC circulation loop, including any cells remaining in the bioreactor, to the harvest bag. Process 1000 then terminates at END operation 1040.

Figure 11:
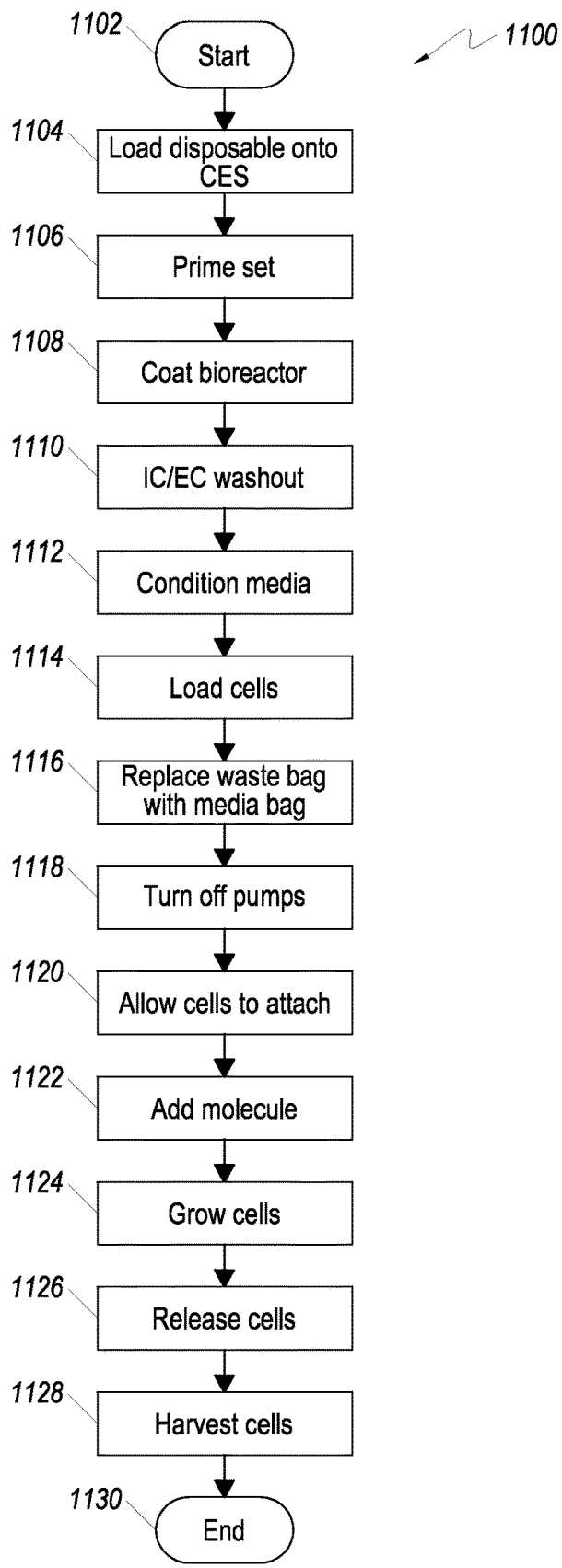
FIG. 11 depicts a flow diagram illustrating the operational characteristics of a process for adding a molecule from a molecule source implemented as part of the cell expansion system itself, in accordance with embodiments of the present disclosure.

Next, FIG. 11 depicts a flow diagram illustrating the operational characteristics of a process 1100 for adding a molecule from a molecule source, implemented as part of a cell expansion system itself, in accordance with embodiments of the present disclosure. While various example embodiments of a cell expansion system and methods for adding a molecule to a cell expansion system have been described, FIG. 11 illustrates example operational steps 1100 for adding a molecule that affects chemical signaling in a closed cell expansion system, in accordance with embodiments of the present disclosure. Some embodiments provide for the passive addition of a molecule from a molecule source. START operation 1102 is initiated, and process 1100 proceeds to load a disposable tubing set 1104 onto the cell expansion system. Next, the system is primed 1106, such as by having an operator or user provide an instruction to the system to prime by selecting a task for priming, for example. In another embodiment, the system is primed 1106 automatically without any selection of a task or instruction from an operator or user.

After priming the set, process 1100 proceeds to coat the bioreactor 1108, in which the bioreactor may be coated with a reagent. For example, in embodiments, a reagent is loaded into the IC loop until a reagent container is empty. The reagent may be chased from the air removal chamber into the IC loop, and the reagent may then be circulated in the IC loop. Once the bioreactor is coated, the IC/EC Washout task may be executed 1110, in which fluid on the IC circulation loop and on the EC circulation loop may be replaced, according to an embodiment. In an embodiment, the replacement volume is determined by the number of IC Volumes and EC Volumes exchanged.

Next, to maintain the proper or desired gas concentration across fibers in the bioreactor membrane, the condition media task 1112 is executed to allow the media to reach equilibrium with the provided gas supply before cells are loaded into the bioreactor. For example, rapid contact between the media and the gas supply provided by the gas transfer module or oxygenator is provided by using a high EC circulation rate. In an embodiment, the system may then be maintained in a proper or desired state until an operator or user is ready to load cells into the bioreactor. In embodiments, such loading of cells is performed automatically.

Process 1100 next proceeds to loading cells into the bioreactor from a cell inlet bag with circulating distribution 1114. In an embodiment, cells are loaded into the bioreactor from a cell inlet bag until the bag is empty. Cells are then chased from the air removal chamber to the bioreactor. In embodiments that utilize larger chase volumes, cells are spread and move toward the IC outlet. The distribution of cells may be promoted across the membrane via IC circulation, such as through the IC circulation pump, with no IC inlet flow, for example.

After completion of the load cells with circulating distribution task 1114, the waste bag is replaced with a media bag 1116. In an embodiment, the media bag comprises about 500 mL of base media. In another embodiment, the media bag comprises any type of replacement fluid. In a further embodiment, step 1116 is optional, in which the outlet or waste bag stays connected and is not replaced with another bag. In yet a further embodiment, step 1116 is optional, in which the outlet or waste bag stays connected and desired constituents or other fluid(s) are added to the outlet or waste bag for passively adding such constituents/other fluid to the system.

In embodiments, one or more pumps, e.g., the IC Inlet Pump, the IC Circulation Pump, and the EC Inlet Pump, may then be turned "OFF" or may otherwise be indicated to stop or deactivate 1118. Any adherent cells in the bioreactor are then allowed to attach to the bioreactor membrane 1120 for a period of time, such as for about eighteen (18) to about twenty-four (24) hours, according to an embodiment of the present disclosure. During this timeframe, flow may continue on the EC circulation loop, in which the EC circulation rate may be maintained at about 30 mL/min, according to an embodiment. A non-zero EC circulation rate helps to maintain the proper or desired gas concentration across the fibers of the bioreactor membrane by continuing to pump fluid in the EC loop through the gas transfer module or oxygenator. While the proper or desired gas concentration is maintained through the use of the gas transfer module, evaporation of fluid also occurs at the gas transfer module. By keeping the EC Waste Valve open, however, media from the substitute media bag (replacing the waste bag) may back-flow into the system and be pumped by the EC Circulation Pump through the EC loop. The media may thus replace fluid lost due to evaporation from the gas transfer module at the rate of evaporation. Thus, membrane fibers in the bioreactor will not be diluted with excess fluid, and the transition of cell growth out of the lag phase will not be inhibited.

After the attaching of any adherent cells, an add molecule phase 1122 is performed. The molecule may be a protein molecule that is added to promote expansion of the cells. For example, the molecule may be a signaling molecule, such as one or more cytokines or growth factors that are involved in intercellular communications. The molecule may signal the cells to expand. In other embodiments, the molecule may not be directly involved in signaling but may help create an environment that is conducive to cell growth, in which examples of such molecules include carrier proteins, buffers, pH modifiers, etc. In embodiments, the molecule is added to the space where the cells are being grown, e.g., the IC or EC space. In embodiments, the molecules are added directly to the IC loop from a direct source of such molecules. Such direct addition may occur at a sampling coil or at a sample port, for example, according to embodiments. Cytokines, or other type of cell-signaling protein molecules, may be added to the bioreactor by, for example, welding a tubing line or other material connected to a cytokine source to a sampling coil or sample coil of the cell expansion system. The cytokines may thus be added to the bioreactor at the sample coil. Such direct addition results in a significant savings of cytokines, which may be costly, because a much higher amount of cytokines would need to be added to a media bag to compensate for dilution of the cytokines by the media than are needed when only the cytokine source itself replenishes the bioreactor, according to an embodiment. Further, cytokines tend to degrade quickly, in which such degradation may be minimized by adding cytokines closer to the expanding cell population, e.g., at the sample coil of the bioreactor itself. In such embodiments, the cytokines in the bioreactor may thus be maintained at a certain level while conserving resources. Through such a source, i.e., direct source, cytokines may be added to the IC loop without diluting such proteins, in which such dilution may occur where the cytokines are added instead at the IC Media bag, for example.

As noted above, the add molecule phase 1122 may be performed after the waste bag is replaced with a media bag 1116, according to an embodiment. In some embodiments, the molecule that is added at operation 1122 may be relatively expensive, and it is desirable to use the minimum amount required to promote growth of the cells. Performing operation 1116 first allows media from the media bag (replacing the waste bag) to back-flow into the system and be pumped by the EC Circulation Pump through the EC loop. According to an embodiment, only the media that is lost due to evaporation from the gas transfer module is replaced and at the rate of evaporation. Thus, the molecule may not be diluted with excess fluid. Accordingly, in an embodiment, only an amount of the molecule that may be effective at promoting growth may be added at operation 1122 since dilution by excess fluid may not be occurring.

After operation 1122, cells are grown at operation 1124. It is noted that, in embodiments, operation 1124 may involve a number of sub-operations. In some embodiments, the sub-operations include operations performed in process 1000 (FIG. 10). For example, in one embodiment, a circulating media operation may be performed to feed the cells. The IC circulation pump may be activated or turned "ON" to provide even the furthest fibers of the bioreactor membrane with media. The IC circulation pump may be activated to adjust the IC circulation rate to about 20 mL/min, according to an embodiment of the present disclosure. In some embodiments, even though the IC circulation pump is turned on, the IC inlet rate remains at 0 mL/min. Rather, the media bag (substitute media bag in replacement of the waste bag) continues to provide any necessary fluid replacement to the system while not diluting the molecule or otherwise inhibiting chemical signaling. In embodiments, operation 1124 allows cell attachment and cell growth to occur without disruption of chemical signaling by dilution of the molecules. This continued cell attachment and growth may continue, according to embodiments, for some predetermined period of time or may be based on a lactate generation of the cells, e.g., 6 mmol/L (in an embodiment). In these embodiments, additional sub-operations, such as determining lactate concentration(s) or that a predetermined period of time has elapsed, may be performed.

Operation 1124 may further involve a sub-operation of activating the IC inlet pump to maintain a predetermined IC inlet rate, e.g., 0.1 mL/min. This sub-operation may be triggered based on a predetermined period of time having elapsed or on a measurement, such as lactate concentration, for example.

In some embodiments, operation 1124 may involve a number of sub-operations to determine when to stop growing cells and begin releasing and harvesting cells. In one embodiment, this may include measuring a parameter, such as glucose consumption. In some embodiments, a predetermined glucose concentration, e.g., greater than 70 mg/L, may trigger subsequent operations, e.g., 1126 and 1128. In other embodiments, other parameters or the passage of a predetermined period of time may trigger subsequent operations.

At operation 1126, any adherent cells are released from the membrane of the bioreactor and are suspended, e.g., in the IC loop. In embodiments, an IC/EC washout task in preparation for adding a reagent to release the cells may be performed as part of operation 1126. For example, IC/EC media may be replaced with PBS to remove protein, calcium ($Ca^{2+}$), and magnesium ($Mg^{2+}$) in preparation for adding trypsin, or other chemical-releasing agent, to release any adherent cells. A reagent may be loaded into the system until the reagent bag is empty. The reagent may be chased into the IC loop, and the reagent may be mixed within the IC loop. Following the release of any adherent cells, harvest operation 1128 transfers the cells in suspension from the IC circulation loop, including any cells remaining in the bioreactor, to a harvest bag(s). Process 1100 then terminates at END operation 1130.

Figure 12:
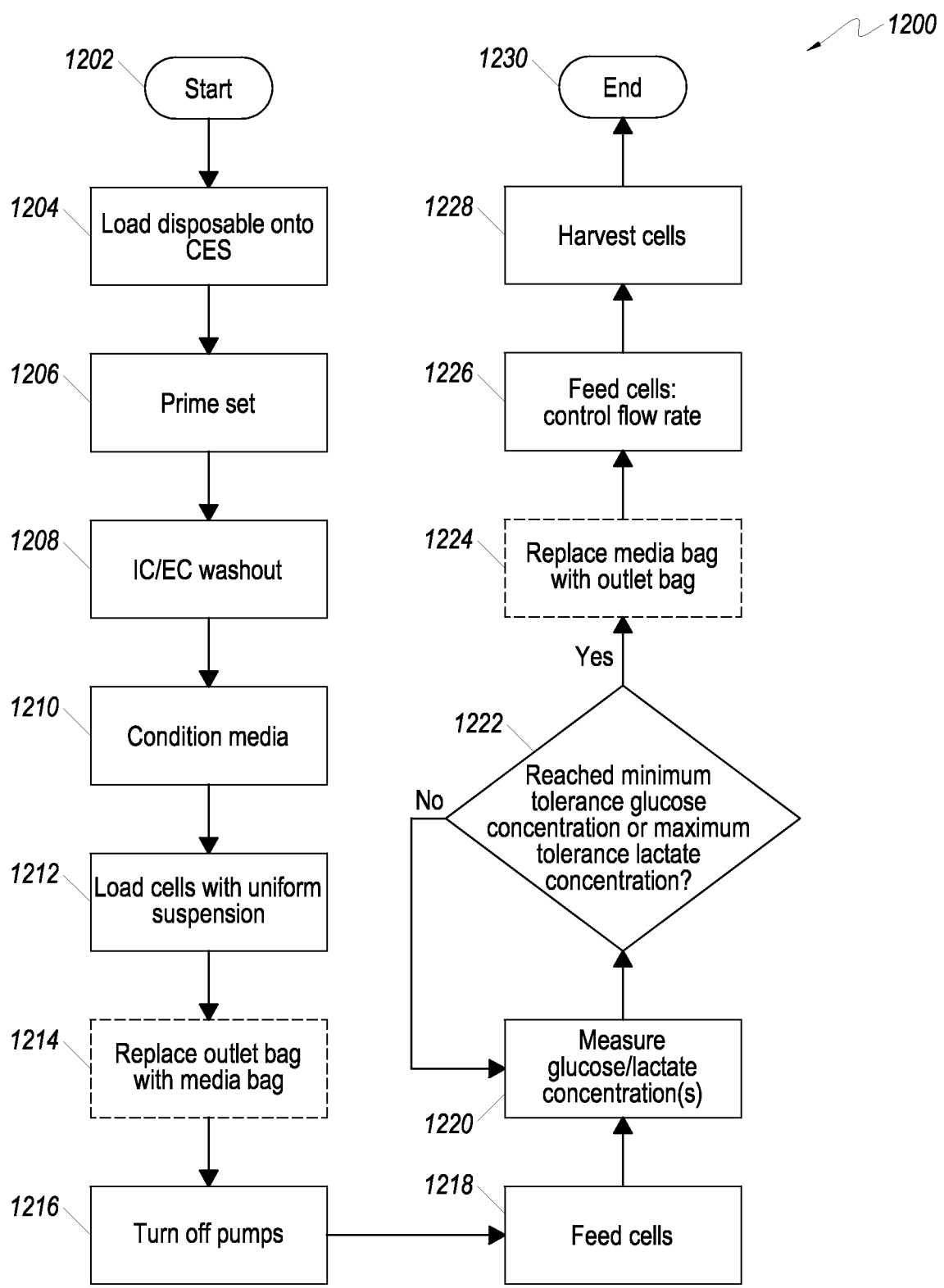
FIG. 12 illustrates a flow diagram depicting the operational characteristics of another embodiment of a process for passively replacing media in a cell expansion system.

Turning to FIG. 12, example operational steps 1200 for passively replacing fluid to control chemical signaling in a closed cell expansion system are shown, in accordance with embodiments of the present disclosure. START operation 1202 is initiated, and process 1200 proceeds to load the disposable tubing set 1204 onto a cell expansion system. Next, the system is primed 1206, such as by having a user or operator instruct the system to prime by selecting a task for priming, for example. In another embodiment, the system is primed 1206 automatically without any selection of a task or instruction from a user or operator. After priming the set, process 1200 proceeds to IC/EC washout 1208, in which fluid on the IC and EC circulation loops may be replaced in preparation for cell culturing. The replacement volume may be specified by the number of IC Volumes and EC Volumes exchanged, according to embodiments. Next, to allow media to reach equilibrium with the gas supply prior to the loading of cells, process 1200 proceeds to condition media task 1210. For example, rapid contact between the media and the gas supply may be provided by using a high EC circulation rate. In an embodiment, the system may then be maintained in a proper state until the user or operator is ready to load cells into the bioreactor. In embodiments, a user or operator may not be needed to perform the noted steps/operations; rather, the steps/operations may be performed automatically by the cell expansion system.

Process 1200 next proceeds to loading cells with uniform suspension 1212. In an embodiment, cells may be loaded from a cell inlet bag. IC circulation may be used to distribute the cells. In an embodiment, cells are loaded into the bioreactor from a cell inlet bag. Cells are then chased from the air removal chamber to the IC loop. The distribution of cells is promoted across the membrane via IC circulation with no IC inlet, for example, and thus no ultrafiltration, according to embodiments.

Next, process 1200 proceeds to the optional (shown in a dashed-line format) step of replacing an outlet or waste bag with a media bag (e.g., a substitute media bag) 1214. In an embodiment, the substitute media bag comprises about 0.2 L of media without protein. Other volumes and types of replacement fluid in the substitute media bag may be used in accordance with embodiments of the present disclosure. Process 1200 next proceeds to turning "OFF" or otherwise deactivating one or more pumps 1216. In an embodiment, the IC inlet pump and the EC inlet pump are turned "OFF" or otherwise indicated to stop or deactivate 1216. Such pump deactivation allows chemical signals, such as CCK, to increase in concentration by turning the inlet media flow rate "OFF" to the IC circulation loop and the EC circulation loop. In such embodiments, fluid from the substitute bag may be passively added to the system at the rate of evaporation during conditions of no active inlet fluid flow. In embodiments where the outlet or waste bag is not replaced, fluid may be passively replaced in the system by interrupting protocol procedures being executed and allowing any fluid in the outlet or waste bag (assuming no constituents toxic to cell growth are present in the outlet or waste bag) to be passively added to the system at the rate of evaporation during conditions of no active inlet fluid flow. Such passive addition of fluid avoids adding an excess amount of fluid and, thus, avoids diluting chemical signaling. In an embodiment, the EC circulation pump may remain "ON." In further embodiments, both the IC circulation pump and the EC circulation pump remain activated or "ON."

Next, process 1200 proceeds to feeding the cells 1218. In an embodiment, the cell culture may be sampled for cell counts as well by excising a length of tubing to provide a representative cell concentration sample of the IC loop. In other embodiments, cells may be counted by withdrawing a sample from the sampling coil or sample port, for example.

Process 1200 next proceeds to measuring the glucose and/or lactate concentration(s) 1220. At query 1222, it is determined whether the cell culture conditions have reached a minimum tolerance glucose concentration or a maximum tolerance lactate concentration. Such tolerance concentrations may occur earlier or later than day 4, according to embodiments. If the tolerance concentration(s) have not been reached, process 1200 proceeds NO to continue to measure the glucose/lactate concentration(s) 1220. If the tolerance concentration(s) have been reached, process 1200 proceeds YES to the optional (shown in a dashed-line format) step of replacing the substitute media bag (from optional step 1214) with the waste or outlet bag 1224. In an embodiment, the original waste or outlet bag removed at optional step 1214 is used to replace the substitute media bag at optional step 1224. In another embodiment, a different waste or media bag is used to replace the substitute media bag at optional step 1224.

Following optional step 1224, process 1200 proceeds to feed the cells by adding a controlled flow rate to the IC circulation loop and/or the EC circulation loop 1226 once the cell culture conditions have reached a minimum tolerance glucose concentration or a maximum tolerance lactate concentration, for example. In an embodiment, a low flow rate is continuously added to the IC circulation loop and/or the EC circulation loop. Such feeding with the continuous addition of a low flow rate, for example, may occur earlier or later than day 4, according to embodiments.

Harvest operation 1228 next transfers cells in suspension from the IC circulation loop, including cells in the bioreactor, to a harvest bag. Process 1200 then terminates at END operation 1230.

With respect to the processes illustrated in FIGS. 10, 11, and 12, the operational steps depicted are offered for purposes of illustration and may be rearranged, combined into other steps, used in parallel with other steps, etc., according to embodiments of the present disclosure. Thus, although the processes have been described with steps listed in a particular order, the present disclosure is not limited to such order. In other embodiments, steps may be performed in a different order, in parallel, or any different number of times, e.g., before and after another step. Further, fewer or additional steps may be used in embodiments without departing from the spirit and scope of the present disclosure. For example, where only suspension or non-adherent cells are present, some steps may not be used as they may be used with adherent cells, such as coating the bioreactor 1008 and 1108, allowing cells to attach 1020 and 1120, and releasing cells 1036 and 1126, for example. Even without such steps, FIGS. 10 and 11, for example, may still apply to the expansion of suspension or non-adherent cells, for example, according to embodiments. As a further example, although not shown in FIGS. 10 and 11, an additional step(s) may include replacing the substitute media bag (previously used to replace the outlet or waste bag) with an outlet or waste bag. Such outlet or waste bag may be the original outlet or waste bag used with the system, according to an embodiment. In another embodiment, a different outlet or waste bag may be used to replace the substitute media bag. Also, the parameters, such as lapse of a predetermined period of time, lactate concentration, glucose consumption, and circulation rates, for example, may also be different than those described above, which are provided merely for illustrative purposes. In addition, as indicated above, process 1200 includes some optional steps/sub-steps shown with dashed-line format. However any steps listed above (in any of processes 1000, 1100, and/or 1200) that are not indicated as optional should not be considered as essential to the one or more present inventions, but may be performed in some embodiments of the one or more present inventions and not in others. Further, while some steps, operations and/or sub-operations are described with reference to an operator or user, such steps, operations and/or sub-operations may be performed automatically, according to embodiments.

Figure 13:
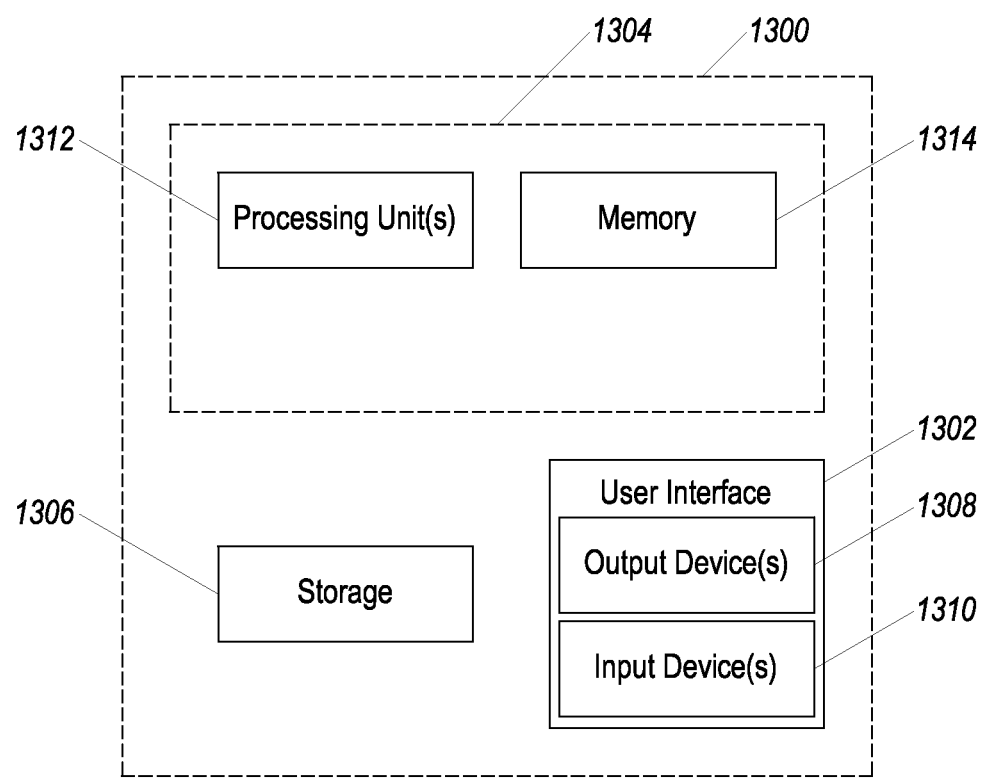
FIG. 13 depicts an example processing system of a cell expansion system upon which embodiments of the present disclosure may be implemented.

Finally, FIG. 13 illustrates example components of a computing system 1300 upon which embodiments of the present disclosure may be implemented. Computing system 1300 may be used in embodiments, for example, where a cell expansion system uses a processor to execute tasks, such as custom tasks or pre-programmed tasks performed as part of processes, such as processes 1000, 1100, and 1200 described above. For example, a pre-programmed task may include, "Feed Cells."

The computing system 1300 may include a user interface 1302, a processing system 1304, and/or storage 1306. The user interface 1302 may include output device(s) 1308, and/or input device(s) 1310 as understood by a person of skill in the art. Output device(s) 1308 may include one or more touch screens, in which the touch screen may comprise a display area for providing one or more application windows. The touch screen may also be an input device 1310 that may receive and/or capture physical touch events from a user or operator, for example. The touch screen may comprise a liquid crystal display (LCD) having a capacitance structure that allows the processing system 1304 to deduce the location(s) of touch event(s), as understood by those of skill in the art. The processing system 1304 may then map the location of touch events to user interface (UI) elements rendered in predetermined locations of an application window. The touch screen may also receive touch events through one or more other electronic structures, according to embodiments. Other output devices 1308 may include a printer, speaker, etc. Other input devices 1310 may include a keyboard, other touch input devices, mouse, voice input device, etc., as understood by a person of skill in the art.

Processing system 1304 may include a processing unit 1312 and/or a memory 1314, according to embodiments of the present disclosure. The processing unit 1312 may be a general purpose processor operable to execute instructions stored in memory 1314. Processing unit 1312 may include a single processor or multiple processors, according to embodiments. Further, in embodiments, each processor may be a multi-core processor having one or more cores to read and execute separate instructions. The processors may include general purpose processors, application specific integrated circuits (ASICs), field programmable gate arrays (FPGAs), other integrated circuits, etc., as understood by a person of skill in the art.

The memory 1314 may include any short-term or long-term storage for data and/or processor executable instructions, according to embodiments. The memory 1314 may include, for example, Random Access Memory (RAM), Read-Only Memory (ROM), or Electrically Erasable Programmable Read-Only Memory (EEPROM), as understood by a person of skill in the art. Other storage media may include, for example, CD-ROM, tape, digital versatile disks (DVD) or other optical storage, tape, magnetic disk storage, magnetic tape, other magnetic storage devices, etc., as understood by a person of skill in the art.

Storage 1306 may be any long-term data storage device or component. Storage 1306 may include one or more of the systems described in conjunction with the memory 1314, according to embodiments. The storage 1306 may be permanent or removable. In embodiments, storage 1306 stores data generated or provided by the processing system 1304.

EXAMPLES

Below are examples of protocols that may be used with a cell expansion system, such as CES 500 (FIG. 5), CES 600

(FIG. 6), CES 700 (FIG. 7), CES 800 (FIG. 8), or CES 900 (FIG. 9), for example, that implements features of this disclosure. It is noted that the example protocols below are provided for illustrative purposes and are not intended to limit other embodiments, which may include different steps, parameters, or other features. The example protocols, including the steps (and any sub-steps) of loading cells and distributing cells, for example, may be performed automatically in some embodiments, such as by a processor executing pre-programmed tasks stored in memory. In other embodiments, the steps (and any sub-steps) are performed through the combination of automated and manual execution of operations. In further embodiments, the steps (and any sub-steps) are performed by an operator(s) or user(s) or through other manual means.

Example 1: Protocol 1

Day: −1 Coat Bioreactor

This part of the example protocol coats a bioreactor with a reagent. The bioreactor may include a hollow fiber membrane.
Step 1: loads a reagent into the IC loop until the bag is empty.
Step 2: chases the reagent from the ARC into the IC loop.
Step 3: circulates the reagent in the IC loop.
Before starting this task, the following preconditions may be satisfied:
Include a minimum of 40 mL of air in the cell inlet bag.
Table 1 describes the bags of solution that are attached to each line when performing the Coat Bioreactor portion of the protocol. These solutions and corresponding volumes are provided as one example of default settings that may be used.

TABLE 1

Solutions for Coat Bioreactor

| Bag | Solution in Bag | Volume (estimation) |
|---|---|---|
| Cell Inlet | None | N/A |
| Reagent | Fibronectin | about 5 mg Fibronectin in about 100 mL PBS |
| IC Media | None | N/A |
| Wash | PBS | about 0.1 L + 6 mL/hr (overnight) |
| EC Media | None | N/A |

The values for each setting for step 1 may be used as shown in Table 2.

TABLE 2

Step 1 for Coat Bioreactor

| Setting | Example Factory Default | Example Laboratory Default | Modifications |
|---|---|---|---|
| IC Inlet | Reagent | | |
| IC Inlet Rate | about 10 mL/min | | |
| IC Circulation Rate | about 100 mL/min | | |
| EC Inlet | None | | |
| EC Inlet Rate | about 0 mL/min | | |
| EC Circulation Rate | about 30 mL/min | | |
| Outlet | EC Waste | | |
| Rocker Control | Stationary, approximately (0°) | | |
| Stop Condition | Empty Bag | | |

Values for each setting for step 2 shown in Table 3 may be used.

TABLE 3

Step 2 Settings for Coat Bioreactor

| Setting | Example Factory Default | Example Laboratory Default | Modifications |
|---|---|---|---|
| IC Inlet | Wash | | |
| IC Inlet Rate | about 10 mL/min | | |
| IC Circulation Rate | about 100 mL/min | | |
| EC Inlet | None | | |
| EC Inlet Rate | about 0 mL/min | | |
| EC Circulation Rate | about 30 mL/min | | |
| Outlet | EC Waste | | |
| Rocker Control | Stationary, approximately (0°) | | |
| Stop Condition | about IC Volume (22 mL) | | |

Values for each setting for step 3 shown in Table 4 may be used.

TABLE 4

Step 3 Settings for Coat Bioreactor

| Setting | Example Factory Default | Example Laboratory Default | Modifications |
|---|---|---|---|
| IC Inlet | None | | |
| IC Inlet Rate | about 0 mL/min | | |
| IC Circulation Rate | about 20 mL/min | | |
| EC Inlet | Wash | | |
| EC Inlet Rate | about 0.1 mL/min | | |
| EC Circulation Rate | about 30 mL/min | | |
| Outlet | EC Waste | | |
| Rocker Control | Stationary, approximately (0°) | | |
| Stop Condition | Manual | | |

Day: 0 IC EC Washout

This part of the example protocol is performed to replace the fluid on both the IC circulation loop and the EC circulation loop. The replacement volume may be specified by the number of IC Volumes and EC Volumes exchanged.

Table 5 describes the bags of solution that are attached to each line when performing IC EC Washout of this example protocol. These solutions and corresponding volumes are provided as one example of default settings that may be used.

TABLE 5

Solutions for IC EC Washout

| Bag | Solution in Bag | Volume (estimation) |
|---|---|---|
| Cell Inlet | None | N/A |
| Reagent | None | N/A |
| IC Media | Media with Protein | about 1.4 L |
| Wash | None | N/A |
| EC Media | None | N/A |

The values for IC EC Washout shown in Table 6 may be used.

TABLE 6

Task Settings for IC EC Washout

| Setting | Example Factory Default | Example Laboratory Default | Modifications |
|---|---|---|---|
| IC Inlet | IC Media | | |
| IC Inlet Rate | about 100 mL/min | | |
| IC Circulation Rate | about −17 mL/min | | |
| EC Inlet | EC Media | | IC Media |
| EC Inlet Rate | about 148 mL/min | | |
| EC Circulation Rate | about −1.7 mL/min | | |
| Outlet | IC and EC Waste | | |
| Rocker Control | In Motion approximately (−90°, 180°, 1 sec) | | |
| Stop Condition | Exchange (about 2.5 IC Volumes) (about 2.5 EC Volumes) | | |

Day: 0 Condition Media

This part of the example protocol is performed to allow the media to reach equilibrium with the provided gas supply before loading the cells. This task may include two separate steps:

Step 1: provides rapid contact between the media and the gas supply by using a high EC circulation rate.

Step 2: maintains the system in a proper state until the operator is ready to load the cells.

Table 7 describes the bags of solution that are attached to each line when performing Condition Media. These solutions and corresponding volumes are provided as one example of default settings that may be used.

TABLE 7

Solutions for Condition Media

| Line | Solution in Bag | Volume (estimation) |
|---|---|---|
| Cell Inlet | None | N/A |
| Reagent | None | N/A |
| IC Media | None | N/A |
| Wash | None | N/A |
| EC Media | Media without Protein | about 0.1 L plus 6 mL/hour |

The values for step 1 shown in Table 8 may be used.

TABLE 8

Step 1 Settings for Condition Media

| Setting | Example Factory Default | Example Laboratory Default | Modifications |
|---|---|---|---|
| IC Inlet | None | | |
| IC Inlet Rate | about 0 mL/min | | |
| IC Circulation Rate | about 100 mL/min | | |
| EC Inlet | EC Media | | IC Media |
| EC Inlet Rate | about 0.1 mL/min | | |
| EC Circulation Rate | about 250 mL/min | | |
| Outlet | EC Waste | | |
| Rocker Control | Stationary, approximately (0°) | | |
| Stop Condition | Time (about 10 min) | | |

The values for step 2 shown in Table 9 may be used.

TABLE 9

Step 2 Settings for Condition Media

| Setting | Example Factory Default | Example Laboratory Default | Modifications |
|---|---|---|---|
| IC Inlet | None | | |
| IC Inlet Rate | 0 | | |
| IC Circulation Rate | about 100 mL/min | | |
| EC Inlet | EC Media | | IC Media |
| EC Inlet Rate | about 0.1 mL/min | | |
| EC Circulation Rate | about 30 mL/min | | |
| Outlet | EC Waste | | |
| Rocker Control | Stationary, approximately (0°) | | |
| Stop Condition | Manual | | |

Day: 0 Load Cells with Circulating Distribution

This part of the example protocol is performed to loads cells into the bioreactor from a cell inlet bag. IC circulation may be used to distribute the cells and may not attempt to chase the cells from the line into the bioreactor. This task may include three separate steps.

Step 1: loads the cells from the cell inlet bag into the bioreactor.

Step 2: chases the cells from the ARC to the bioreactor. Larger chase volumes spread the cells and move them towards the IC outlet.

Step 3: promotes distribution of cells across membrane via IC circulation and no IC inlet thus no ultrafiltration.

Before starting this task, the following preconditions may be satisfied:

Include a minimum of 40 mL of air in the cell inlet bag.

Table 10 describes the bags of solution attached to each line when performing Load Cells with Circulating Distribution. These solutions and corresponding volumes are provided as one example of default settings that may be used.

TABLE 10

Solutions for Load Cells With Circulating Distribution

| Line | Solution in Bag | Volume (estimation) |
|---|---|---|
| Cell Inlet | Cells | Cells in about 100 mL complete media |
| Reagent | None | N/A |
| IC Media | Media with Protein | about 0.1 L |
| Wash | None | N/A |
| EC Media | None | N/A |

The values for step 1 shown in Table 11 may be used.

TABLE 11

Step 1 Settings for Load Cells With Circulating Distribution

| Setting | Example Factory Default | Example Laboratory Default | Modifications |
|---|---|---|---|
| IC Inlet | None | | Cells |
| IC Inlet Rate | about 0 mL/min | | about 25 mL/min |
| IC Circulation Rate | about 0 mL/min. | | about 150 mL/min |
| EC Inlet | None | | |
| EC Inlet Rate | about 0 mL/min | | |

TABLE 11-continued

Step 1 Settings for Load Cells With Circulating Distribution

| Setting | Example Factory Default | Example Laboratory Default | Modifications |
|---|---|---|---|
| EC Circulation Rate | about 0 mL/min | | about 30 mL/min |
| Outlet | EC Waste | | |
| Rocker Control | Stationary, approximately | | In Motion, approximately (−90°, 180°, 1 sec) |
| Stop Condition | Manual | | Empty Bag |

The values for step 2 shown in Table 12 may be used.

TABLE 12

Step 2 Settings for Load Cells with Circulating Distribution

| Setting | Example Factory Default | Example Laboratory Default | Modifications |
|---|---|---|---|
| IC Inlet | None | | IC Media |
| IC Inlet Rate | about 0 mL/min | | about 25 mL/min |
| IC Circulation Rate | about 0 mL/min. | | about 150 mL/min |
| EC Inlet | None | | |
| EC Inlet Rate | about 0 mL/min | | |
| EC Circulation Rate | about 0 mL/min | | about 30 mL/min |
| Outlet | EC Waste | | |
| Rocker Control | Stationary, approximately | | In Motion, approximately (−90°, 180°, 1 sec) |
| Stop Condition | Manual | | IC Volume (about 47 mL) |

The values for step 3 shown in Table 13 may be used.

TABLE 13

Step 3 Settings for Load Cells with Circulating Distribution

| Setting | Factory Default | Laboratory Default | Modifications |
|---|---|---|---|
| IC Inlet | None | | |
| IC Inlet Rate | about 0 mL/min | | |
| IC Circulation Rate | about 0 mL/min. | | about 200 mL/min |
| EC Inlet | None | | |
| EC Inlet Rate | about 0 mL/min | | |
| EC Circulation Rate | about 0 mL/min | | about 30 mL/min |
| Outlet | EC Waste | | |
| Rocker Control | Stationary, approximately | | In Motion, approximately (−90°, 180°, 1 sec) |
| Stop Condition | Manual | | Time (about 2.0 min) |

Day: 0 Attach Cells

This part of the example protocol is performed to enable adherent cells to attach to the bioreactor membrane while allowing flow on the EC circulation loop. The pump flow rate to the IC loop is set to approximately zero.

Table 14 describes the bags of solution attached to each line when performing Attach Cells. These solutions and corresponding volumes are provided as one example of default settings that may be used.

TABLE 14

Solutions for Attach Cells

| Bag | Solution in Bag | Volume (estimation based on factory default values) |
|---|---|---|
| Cell Inlet | None | N/A |
| Reagent | None | N/A |
| IC Media | None | N/A |
| Wash | None | N/A |
| EC Media | None | N/A |
| Waste | Base Media | 500 mL |

The values for Attach Cells shown in Table 15 may be used.

TABLE 15

Task Settings for Attach Cells

| Setting | Example Factory Default | Example Laboratory Default | Modifications |
|---|---|---|---|
| IC Inlet | None | | |
| IC Inlet Rate | about 0 mL/min | | |
| IC Circulation Rate | about 0 mL/min | | |
| EC Inlet | EC Media | None | |
| EC Inlet Rate | about 0.1 mL/min | 0 | |
| EC Circulation Rate | about 30 mL/min | | |
| Outlet | EC Waste | | |
| Rocker Control | Stationary, approximately (0°) | | |
| Stop Condition | Manual | | |

Day: 1 Feed Cells

This part of the example protocol is performed to continuously add a low flow rate to the IC circulation loop and/or the EC circulation loop. There are several outlet settings that may used to remove the fluid added to the system.

Table 16 describes the bags of solution attached to each line when performing Feed Cells. These solutions and corresponding volumes are provided as one example of default settings that may be used.

TABLE 16

Solutions for Feed Cells

| Bag | Solution in Bag | Volume (estimation) |
|---|---|---|
| Cell Inlet | None | N/A |
| Reagent | None | N/A |
| IC Media | Media with Protein | about 6 mL/hour |
| Wash | None | N/A |
| EC Media | None | N/A |
| Waste | Base Media | about 500 mL |

The values for step 1 shown in Table 17 may be used.

TABLE 17

Task Settings for Feed Cells

| Setting | Example Factory Default | Example Laboratory Default | Modifications |
|---|---|---|---|
| IC Inlet | IC Media | | |
| IC Inlet Rate | about 0.1 mL/min | 0 mL/min | |

TABLE 17-continued

Task Settings for Feed Cells

| Setting | Example Factory Default | Example Laboratory Default | Modifications |
|---|---|---|---|
| IC Circulation Rate | about 20 mL/min | | |
| EC Inlet | None | | |
| EC Inlet Rate | about 0 mL/min | | |
| EC Circulation Rate | about 30 mL/min | | |
| Outlet | IC Waste | | |
| Rocker Control | Stationary, approximately (0°) | | |
| Stop Condition | Manual | | |

The IC Inlet rate may be increased as needed. As one example, the IC inlet rate may be increased as follows: Day 1-Day 2: 0.0 mL/min; Day 2-Day 3: 0.1 mL/min; Day 3-Day 4: 0.2 mL/min; Day 4-Day 5: 0.4 mL/min; and Day 5-Day 6: 0.8 mL/min.

Release Adherent Cells

This part of the example protocol is performed to release cells from the membrane, leaving the cells in the IC loop.

Step 1: performs the IC/EC Washout task in preparation for adding a reagent. For example, the system replaces IC/EC media with PBS to remove protein, Ca++, and Mg++ in preparation for adding trypsin.

Step 2: loads a reagent into the system until the bag is empty.

Step 3: chases the reagent into the IC loop.

Step 4: mixes the reagent within the IC loop.

Before starting this task, the following preconditions may be satisfied:

Include a minimum of 40 mL of air in the cell inlet bag.

Table 18 describes the bags of solution attached to each line when performing Release Adherent Cells. These solutions and corresponding volumes are provided as one example of default settings that may be used.

TABLE 18

Solutions for Release Adherent Cells

| Bag | Solution in Bag | Volume (estimation) |
|---|---|---|
| Cell Inlet | None | N/A |
| Reagent | Trypsin | about 180 mL |
| IC Media | None | N/A |
| Wash | PBS | about 1.4 L |
| EC Media | None | N/A |

The values for step 1 shown in Table 19 may be used.

TABLE 19

Step 1 Settings for Release Adherent Cells

| Setting | Example Factory Default | Example Laboratory Default | Modifications |
|---|---|---|---|
| IC Inlet | Wash | | |
| IC Inlet Rate | about 100 mL/min | | |
| IC Circulation Rate | about −17 mL/min | | |
| EC Inlet | Wash | | |
| EC Inlet Rate | about 148 mL/min | | |
| EC Circulation Rate | about −1.7 mL/min | | |
| Outlet | IC and EC Waste | | |
| Rocker Control | In Motion, approximately (−90°, 180°, 1 sec) | | |
| Stop Condition | Exchange (about 2.5 IC Volumes) (about 2.5 EC Volumes) | | |

The values for step 2 shown in Table 20 may be used.

TABLE 20

Step 2 Settings for Release Adherent Cells

| Setting | Example Factory Default | Example Laboratory Default | Modifications |
|---|---|---|---|
| IC Inlet | Reagent | | |
| IC Inlet Rate | about 50 mL/min | | |
| IC Circulation Rate | about 300 mL/min | | |
| EC Inlet | None | | |
| EC Inlet Rate | about 0 mL/min | | |
| EC Circulation Rate | about 30 mL/min | | |
| Outlet | EC Waste | | |
| Rocker Control | In Motion, approximately (−90°, 180°, 1 sec) | | |
| Stop Condition | Empty Bag | | |

The values for step 3 shown in Table 21 may be used.

TABLE 21

Step 3 Settings for Release Adherent Cells

| Setting | Example Factory Default | Example Laboratory Default | Modifications |
|---|---|---|---|
| IC Inlet | Wash | | |
| IC Inlet Rate | about 50 mL/min | | |
| IC Circulation Rate | about 300 mL/min | | |
| EC Inlet | None | | |
| EC Inlet Rate | about 0 mL/min | | |
| EC Circulation Rate | about 30 mL/min | | |
| Outlet | EC Waste | | |
| Rocker Control | In Motion, approximately (−90°, 180°, 1 sec) | | |
| Stop Condition | IC Volume (22 mL) | | |

The values for step 4 shown in Table 22 may be used.

TABLE 22

Step 4 Settings for Release Adherent Cells

| Setting | Example Factory Default | Example Laboratory Default | Modifications |
|---|---|---|---|
| IC Inlet | None | | |
| IC Inlet Rate | about 0 mL/min | | |
| IC Circulation Rate | about 300 mL/min | | |
| EC Inlet | None | | |
| EC Inlet Rate | about 0 mL/min | | |
| EC Circulation Rate | about 30 mL/min | | |

TABLE 22-continued

Step 4 Settings for Release Adherent Cells

| Setting | Example Factory Default | Example Laboratory Default | Modifications |
|---|---|---|---|
| Outlet | EC Waste | | |
| Rocker Control | In Motion, approximately (−90°, 180°, 1 sec) | | |
| Stop Condition | Time (about 4 min) | | |

Samples may be taken from a sample coil and/or a sample port for a trypsin assay.

Harvest Cells

This part of the example protocol is performed to transfer cells in suspension from the IC circulation loop, including cells in the bioreactor, to the harvest bag.

Table 23 describes the bags of solution attached to each line when performing Harvest Cells. These solutions and corresponding volumes are provided as one example of default settings that may be used.

TABLE 23

Solutions for Harvest Cells

| Bag | Solution in Bag | Volume (estimation) |
|---|---|---|
| Cell Inlet | None | N/A |
| Reagent | None | N/A |
| IC Media | Harvest Media | about 0.6 L |
| Wash | None | N/A |
| EC Media | None | N/A |

The values for Harvest Cells shown in Table 24 may be used.

TABLE 24

Task Settings for Harvest Cells

| Setting | Example Factory Default | Example Laboratory Default | Modifications |
|---|---|---|---|
| IC Inlet | IC Media | | |
| IC Inlet Rate | about 400 mL/min | | |
| IC Circulation Rate | about −69 mL/min | | |
| EC Inlet | EC Media | IC Media | |
| EC Inlet Rate | about 60 mL/min | | |
| EC Circulation Rate | about 30 mL/min | | |
| Outlet | Harvest | | |
| Rocker Control | In Motion, approximately (−90°, 180°, 1 sec) | | |
| Stop Condition | IC Volume (about 378 mL) | | |

Example 2: Protocol 2

Cholecystokinin (CCK) is a regulatory hormone secreted by cells and, in many cases, may in part be responsible for cell culture maintenance and proliferation via chemical signaling. If CCK concentration in the culture media does not reach a threshold, the cell population can be compromised. Example 2 provides an example of a cell-secreted chemical signal used to maintain and proliferate a population of cells in vitro; in this case, CHO cells. According to an embodiment, the molecular weight of CCK of approximately 4,000 Daltons makes it small enough to readily pass through the microporous membrane of a hollow-fiber bioreactor. In an embodiment, regardless of inlet media addition to the IC circulation loop or EC circulation loop, dilution of the chemical signal may occur due to the freedom to pass through the membrane. However, through the passive replacement of media, according to embodiments, such dilution of chemical signaling can be minimized or eliminated altogether. The following protocol provides for the passive replacement of media during the cell expansion of non-adherent or suspension cells, such as CHO cells, for example, according to embodiments.

Day: 0 IC EC Washout

This part of the example protocol is performed to replace the fluid on both the IC circulation loop and the EC circulation loop in preparation for cell culturing. The replacement volume may be specified by the number of IC Volumes and EC Volumes exchanged.

Table 25 describes the bags of solution that are attached to each line when performing IC EC Washout of this example protocol. These solutions and corresponding volumes are provided as one example of default settings that may be used.

TABLE 25

Solutions for IC EC Washout

| Bag | Solution in Bag | Volume (estimation) |
|---|---|---|
| Cell Inlet | None | N/A |
| Reagent | None | N/A |
| IC Media | Media without Protein | about 1.4 L |
| Wash | None | N/A |
| EC Media | None | N/A |

The values for IC EC Washout shown in Table 26 may be used.

TABLE 26

Task Settings for IC EC Washout

| Setting | Example Factory Default | Example Laboratory Default | Modifications |
|---|---|---|---|
| IC Inlet | IC Media | | |
| IC Inlet Rate | about 100 mL/min | | |
| IC Circulation Rate | about −17 mL/min | | |
| EC Inlet | EC Media | IC Media | |
| EC Inlet Rate | about 148 mL/min | | |
| EC Circulation Rate | about −1.7 mL/min | | |
| Outlet | IC and EC Waste | | |
| Rocker Control | In Motion approximately (−90°, 180°, 1 sec) | | |
| Stop Condition | Exchange (about 2.5 IC Volumes) (about 2.5 EC Volumes) | | |

Day: 0 Condition Media

This part of the example protocol is performed to allow the media to reach equilibrium with the provided gas supply before loading the cells. This task may include two separate steps:

Step 1: provides rapid contact between the media and the gas supply by using a high EC circulation rate.

Step 2: maintains the system in a proper state until the operator is ready to load the cells.

Table 27 describes the bags of solution that are attached to each line when performing Condition Media. These solutions and corresponding volumes are provided as one example of default settings that may be used.

TABLE 27

Solutions for Condition Media

| Line | Solution in Bag | Volume (estimation) |
|---|---|---|
| Cell Inlet | None | N/A |
| Reagent | None | N/A |
| IC Media | Media without Protein | about 0.1 L plus 6 mL/hour |
| Wash | None | N/A |
| EC Media | None | N/A |

The values for step 1 shown in Table 28 may be used.

TABLE 28

Step 1 Settings for Condition Media

| Setting | Example Factory Default | Example Laboratory Default | Modifications |
|---|---|---|---|
| IC Inlet | None | | |
| IC Inlet Rate | about 0 mL/min | | |
| IC Circulation Rate | about 100 mL/min | | |
| EC Inlet | EC Media | IC Media | |
| EC Inlet Rate | about 0.1 mL/min | | |
| EC Circulation Rate | about 250 mL/min | | |
| Outlet | EC Waste | | |
| Rocker Control | Stationary, approximately (0°) | | |
| Stop Condition | Time (about 10 min) | | |

The values for step 2 shown in Table 29 may be used.

TABLE 29

Step 2 Settings for Condition Media

| Setting | Example Factory Default | Example Laboratory Default | Modifications |
|---|---|---|---|
| IC Inlet | None | | |
| IC Inlet Rate | 0 | | |
| IC Circulation Rate | about 100 mL/min | | |
| EC Inlet | EC Media | IC Media | |
| EC Inlet Rate | about 0.1 mL/min | | |
| EC Circulation Rate | about 30 mL/min | | |
| Outlet | EC Waste | | |
| Rocker Control | Stationary, approximately (0°) | | |
| Stop Condition | Manual | | |

Day: 0 Load Cells with Uniform Suspension

This part of the example protocol is performed to load cells into the bioreactor from a cell inlet bag. For example, in an embodiment, such cells comprise CHO cells. IC circulation may be used to distribute the cells and may not attempt to chase the cells from the line into the bioreactor. This task may include three separate steps.

Step 1: loads the cells from the cell inlet bag into the bioreactor.

Step 2: chases the cells from the ARC to the IC Loop.

Step 3: promotes distribution of cells across membrane via IC circulation and no IC inlet, thus no ultrafiltration.

Before starting this task, the following preconditions may be satisfied:

Include a minimum of 40 mL of air in the cell inlet bag.

Table 30 describes the bags of solution attached to each line when performing Load Cells with Uniform Suspension. These solutions and corresponding volumes are provided as one example of default settings that may be used.

TABLE 30

Solutions for Load Cells with Uniform Suspension

| Line | Solution in Bag | Volume (estimation) |
|---|---|---|
| Cell Inlet | Cells | 9.45E+07 Cells in about 100 mL media |
| Reagent | None | N/A |
| IC Media | Media without Protein | about 0.1 L |
| Wash | None | N/A |
| EC Media | None | N/A |

The values for step 1 shown in Table 31 may be used.

TABLE 31

Step 1 Settings for Load Cells with Uniform Suspension

| Setting | Example Factory Default | Example Laboratory Default | Modifications |
|---|---|---|---|
| IC Inlet | Cell Inlet | | |
| IC Inlet Rate | about 50 mL/min | | |
| IC Circulation Rate | about 200 mL/min. | | |
| EC Inlet | None | | |
| EC Inlet Rate | about 0 mL/min | | |
| EC Circulation Rate | about 30 mL/min | | |
| Outlet | EC Outlet | | |
| Rocker Control | In Motion, approximately (−90°, 180°, 1 sec) | | |
| Stop Condition | Empty Bag | | |

The values for step 2 shown in Table 32 may be used.

TABLE 32

Step 2 Settings for Load Cells with Uniform Suspension

| Setting | Example Factory Default | Example Laboratory Default | Modifications |
|---|---|---|---|
| IC Inlet | IC Media | | |
| IC Inlet Rate | about 50 mL/min | | |
| IC Circulation Rate | about 200 mL/min | | |
| EC Inlet | None | | |
| EC Inlet Rate | about 0 mL/min | | |
| EC Circulation Rate | about 30 mL/min | | |
| Outlet | EC Outlet | | |
| Rocker Control | In Motion (−90°, 180°, 1 sec) | | |
| Stop Condition | IC Volume (about 22 mL) | | |

The values for step 3 shown in Table 33 may be used.

TABLE 33

Step 3 Settings for Load Cells with Uniform Suspension

| Setting | Factory Default | Laboratory Default | Modifications |
|---|---|---|---|
| IC Inlet | None | | |
| IC Inlet Rate | about 0 mL/min | | |
| IC Circulation Rate | about 200 mL/min | | |
| EC Inlet | None | | |
| EC Inlet Rate | about 0 mL/min | | |
| EC Circulation Rate | about 30 mL/min | | |
| Outlet | EC Outlet | | |
| Rocker Control | In Motion (−90°, 180°, 1 sec) | | |
| Stop Condition | Time (about 2.0 min) | | |

Day: 0 Feed Cells

This part of the example protocol is performed to allow chemical signals, such as CCK, to increase in concentration by turning the inlet media flow rate "OFF" to the IC circulation loop and the EC circulation loop. IC or EC Outlet can be used in this configuration.

Table 34 describes the bags of solution attached to each line when performing Feed Cells. These solutions and corresponding volumes are provided as one example of default settings that may be used.

TABLE 34

Solutions for Feed Cells

| Bag | Solution in Bag | Volume (estimation) |
|---|---|---|
| Cell Inlet | None | N/A |
| Reagent | None | N/A |
| IC Media | None | N/A |
| Wash | None | N/A |
| EC Media | None | N/A |
| Outlet | Media without Protein | 0.2 L |

The values for step 1 shown in Table 35 may be used.

TABLE 35

Task Settings for Feed Cells

| Setting | Example Factory Default | Example Laboratory Default | Modifications |
|---|---|---|---|
| IC Inlet | IC Media | | None |
| IC Inlet Rate | about 0.1 mL/min | | about 0 mL/min |
| IC Circulation Rate | about 20 mL/min | | about 50 mL/min |
| EC Inlet | None | | |
| EC Inlet Rate | about 0 mL/min | | |
| EC Circulation Rate | about 30 mL/min | | |
| Outlet | IC Outlet | | EC Outlet |
| Rocker Control | Stationary, approximately (0°) | | In Motion (0°, 180°, about 60 sec) |
| Stop Condition | Manual | | |

In an embodiment, each day, the cell culture is sampled for cell counts using the following settings:

TABLE 36

Task Settings for Counting Cells

| Setting | Example Factory Default | Example Laboratory Default | Modifications |
|---|---|---|---|
| IC Inlet | None | | |
| IC Inlet Rate | about 0 mL/min | | |
| IC Circulation Rate | about 200 mL/min | | |
| EC Inlet | None | | |
| EC Inlet Rate | about 0 mL/min | | |
| EC Circulation Rate | about 30 mL/min | | |
| Outlet | IC Outlet | | EC Outlet |
| Rocker Control | In Motion (0°, 180°, 1 sec) | | |
| Stop Condition | Time (about 5.0 min) | | |

In an embodiment, immediately following the stop condition, a length of tubing of about six (6) inches long (1 mL) is excised. The volume in this sample provides a representative cell concentration sample of the entire IC loop. This allows the user(s) to monitor the cells throughout the duration of culturing.

Day: 4 Feed Cells

This part of the example protocol is performed to continuously add a low flow rate to the IC circulation loop and/or the EC circulation loop once the cell culture conditions have reached a minimum tolerance glucose concentration or maximum tolerance lactate concentration. This may occur earlier or later than day 4, in embodiments. There are several outlet settings that may used to remove the fluid added to the system.

Table 37 describes the bags of solution attached to each line when performing Feed Cells. These solutions and corresponding volumes are provided as one example of default settings that may be used.

TABLE 37

Solutions for Feed Cells

| Bag | Solution in Bag | Volume (estimation) |
|---|---|---|
| Cell Inlet | None | N/A |
| Reagent | None | N/A |
| IC Media | Media without Protein | about 6 mL/hour |
| Wash | None | N/A |
| EC Media | None | N/A |

The values for step 1 shown in Table 38 may be used.

TABLE 38

Task Settings for Feed Cells

| Setting | Example Factory Default | Example Laboratory Default | Modifications |
|---|---|---|---|
| IC Inlet | IC Media | | |
| IC Inlet Rate | about 0.1 mL/min | | |
| IC Circulation Rate | about 20 mL/min | | about 50 mL/min |
| EC Inlet | None | | |
| EC Inlet Rate | about 0 mL/min | | |
| EC Circulation Rate | about 30 mL/min | | |
| Outlet | IC Outlet | | EC Outlet |

TABLE 38-continued

Task Settings for Feed Cells

| Setting | Example Factory Default | Example Laboratory Default | Modifications |
|---|---|---|---|
| Rocker Control | Stationary, approximately (0°) | | In Motion (0°, 180°, about 60 sec) |
| Stop Condition | Manual | | |

In an embodiment, each day, the cell culture is sampled for cell counts (see Table 36, for example).

Day: 7 Harvest Cells

This part of the example protocol is performed to transfer cells in suspension from the IC circulation loop, including cells in the bioreactor, to the harvest bag.

Table 39 describes the bags of solution attached to each line when performing Harvest Cells. These solutions and corresponding volumes are provided as one example of default settings that may be used.

TABLE 39

Solutions for Harvest Cells

| Bag | Solution in Bag | Volume (estimation) |
|---|---|---|
| Cell Inlet | None | N/A |
| Reagent | None | N/A |
| IC Media | Harvest Media | about 0.6 L |
| Wash | None | N/A |
| EC Media | None | N/A |

The values for Harvest Cells shown in Table 40 may be used.

TABLE 40

Task Settings for Harvest Cells

| Setting | Example Factory Default | Example Laboratory Default | Modifications |
|---|---|---|---|
| IC Inlet | IC Media | | |
| IC Inlet Rate | about 400 mL/min | | |
| IC Circulation Rate | about −69 mL/min | | |
| EC Inlet | EC Media | | IC Media |
| EC Inlet Rate | about 60 mL/min | | |
| EC Circulation Rate | about 30 mL/min | | |
| Outlet | Harvest | | |
| Rocker Control | In Motion, approximately (−90°, 180°, 1 sec) | | |
| Stop Condition | IC Volume (about 378 mL) | | |

It will be apparent to those skilled in the art that various modifications and variations may be made to the apparatus, systems, structure, and methods described herein. Thus, it should be understood that the embodiments are not limited to the subject matter discussed in the present disclosure. Rather, the present disclosure is intended to cover modifications, variations, and/or equivalents. The acts, features, structures, and/or media are disclosed as illustrative embodiments for implementation of the claims.

What is claimed is:

1. A method for controlling chemical signaling during an expansion of cells in a bioreactor of a closed cell expansion system, the method comprising:
performing a first portion of a protocol for the expansion of the cells with the cell expansion system arranged in a first configuration, wherein the first configuration comprises:
a first media bag connected to an attachment point, wherein the attachment point is fluidly associated with a first fluid flow path, and wherein the first fluid flow path is fluidly associated with the bioreactor;
a first outlet bag connected, via an extracapillary waste valve, to an outlet line, wherein the outlet line is connected to an extracapillary circulation path of the bioreactor;
and wherein performing the first portion of the protocol comprises:
coating the bioreactor;
loading the cells into the bioreactor, wherein the cells are loaded from a cell inlet bag into the bioreactor;
activating an intracapillary inlet pump and an intracapillary circulation pump to introduce a first media from the first media bag into the bioreactor;
activating an extracapillary inlet pump;
activating an extracapillary circulation pump to circulate a fluid in the extracapillary circulation path through a gas transfer module, wherein an amount of the fluid in the extracapillary circulation path evaporates at a rate of evaporation;
performing a second portion of the protocol with the cell expansion system arranged in a second configuration, wherein the second portion of the protocol is performed after the first portion of the protocol, and comprises:
disconnecting the first outlet bag from the outlet line;
connecting a second media bag, via the extracapillary waste valve, to the outlet line, wherein the second media bag replaces the first outlet bag;
deactivating the intracapillary inlet pump;
deactivating the intracapillary circulation pump;
deactivating the extracapillary inlet pump; and
introducing, through the outlet line, into the extracapillary circulation path, a second media from the second media bag into the extracapillary circulation path, wherein the second media is introduced at the rate of evaporation of the fluid in the extracapillary circulation path.

2. The method of claim 1, wherein the second media from the second media bag flows through the extracapillary waste valve to the extracapillary circulation path, and wherein the performing the second portion of the protocol further comprises:
maintaining the extracapillary circulation pump in an activated state; and
maintaining the extracapillary waste valve in an open position.

3. The method of claim 2, wherein the cells comprise adherent cells, and wherein performing the second portion of the protocol further comprises:
enabling the adherent cells to attach to a membrane of the bioreactor for a period of time of about eighteen hours to about twenty-four hours;
maintaining flow in the extracapillary circulation path by the maintaining the extracapillary circulation pump in the activated state;
after the period of time of about eighteen hours to about twenty-four hours, feeding the cells in the bioreactor through the outlet line with the second media from the second media bag, wherein the feeding comprises:
re-activating the intracapillary circulation pump.

4. The method of claim 3, wherein performing the second portion of the protocol further comprises:
after about forty-five hours to about fifty hours of feeding the cells in the bioreactor through the outlet line, stopping the feeding of the cells through the outlet line.

5. The method of claim 3, wherein performing the second portion of the protocol further comprises:
after about forty-eight hours of feeding the cells in the bioreactor through the outlet line, stopping the feeding of the cells through the outlet line.

6. The method of claim 3, wherein performing the second portion of the protocol further comprises:
measuring a concentration of lactate generated from the cells;
stopping the feeding of the cells in the bioreactor through the outlet line when the concentration of the lactate is equal to or greater than about 6 mmol/L;
after stopping the feeding of the cells in the bioreactor through the outlet line:
disconnecting the second media bag from the outlet line;
connecting a second outlet bag, via the extracapillary waste valve, to the outlet line, wherein the second outlet bag replaces the second media bag;
re-activating the intracapillary inlet pump, wherein the intracapillary inlet pump operates at an intracapillary inlet rate of about 0.1 mL/min;
operating the intracapillary circulation pump at an intracapillary circulation rate of about 20 mL/min;
operating the extracapillary circulation pump at an extracapillary circulation rate of about 30 mL/min;
doubling the intracapillary inlet rate until a desired number of the cells is available for harvest; and
when the desired number of the cells is available for harvest:
releasing the cells from the membrane of the bioreactor;
suspending the cells in an intracapillary circulation path; and
transferring the cells in suspension to a harvest bag.

7. The method of claim 3, wherein feeding the cells in the bioreactor through the outlet line with the second media comprises feeding the cells without operating an inlet pump to introduce the second media into the bioreactor.

8. The method of claim 1, wherein the steps of coating the bioreactor and loading the cells are performed by a processor executing pre-programmed tasks stored in memory.

9. The method of claim 1, wherein replacement of the first outlet bag with the second media bag is performed manually.

10. The method of claim 1, wherein replacement of the first outlet bag with the second media bag is performed automatically.

11. The method of claim 1, wherein the second media bag comprises base media.

12. The method of claim 11, wherein the second media bag comprises about 500 mL of base media.

13. The method of claim 1, further comprising:
loading cell-signaling protein molecules into an intracapillary circulation path.

14. The method of claim 13, wherein the cell-signaling protein molecules are loaded into a sampling coil of the intracapillary circulation path, and wherein the sampling coil and the intracapillary circulation path are part of a disposable tubing set.

15. The method of claim 13, wherein the cell-signaling protein molecules are loaded into a sample port of the intracapillary circulation path.

16. The method of claim 1, wherein performing the first portion of the protocol further comprises:
distributing the cells across a membrane of the bioreactor, wherein distributing the cells occurs by activating the intracapillary circulation pump.

17. The method of claim 1, wherein the second media bag comprises cell-signaling protein molecules.

18. The method of claim 17, wherein performing the second portion of the protocol further comprises:
adding the cell-signaling protein molecules from the second media bag at the first rate of evaporation of the fluid in the extracapillary circulation path.

19. The method of claim 1, wherein the outlet line is a waste line.

20. The method of claim 1, wherein the second media bag comprises base media and glucose.

* * * * *